(12) United States Patent
Hecht et al.

(10) Patent No.: US 12,383,629 B2
(45) Date of Patent: Aug. 12, 2025

(54) DNA-AFFIBODY-DRUG NANOPARTICLES FOR INHIBITING THE METASTASIS OF CANCER CELLS OVEREXPRESSING HER2

(71) Applicant: Arizona Board of Regents on behalf of Arizona State University, Scottsdale, AZ (US)

(72) Inventors: Sidney Hecht, Phoenix, AZ (US); Shengxi Chen, Chandler, AZ (US)

(73) Assignee: Arizona Board of Regents on behalf of Arizona State University, Scottsdale, AZ (US)

(*) Notice: Subject to any disclaimer, the term of this patent is extended or adjusted under 35 U.S.C. 154(b) by 780 days.

(21) Appl. No.: 17/630,994

(22) PCT Filed: Jul. 22, 2020

(86) PCT No.: PCT/US2020/043099
§ 371 (c)(1),
(2) Date: Jan. 28, 2022

(87) PCT Pub. No.: WO2021/021523
PCT Pub. Date: Feb. 4, 2021

(65) Prior Publication Data
US 2022/0265838 A1    Aug. 25, 2022

Related U.S. Application Data

(60) Provisional application No. 62/880,272, filed on Jul. 30, 2019.

(51) Int. Cl.
| | |
|---|---|
| *A61K 47/64* | (2017.01) |
| *A61K 31/65* | (2006.01) |
| *A61K 47/54* | (2017.01) |
| *A61P 35/00* | (2006.01) |
| *A61P 35/04* | (2006.01) |
| *C07K 14/00* | (2006.01) |
| *C12N 15/11* | (2006.01) |

(52) U.S. Cl.
CPC .............. *A61K 47/64* (2017.08); *A61K 31/65* (2013.01); *A61K 47/549* (2017.08); *A61P 35/00* (2018.01); *A61P 35/04* (2018.01); *C07K 14/00* (2013.01); *C12N 15/11* (2013.01); *C12N 2310/3513* (2013.01); *C12N 2310/50* (2013.01)

(58) Field of Classification Search
CPC ...... A61K 47/64; A61K 47/549; A61K 31/65; A61P 35/04; A61P 35/00; C07K 14/00; C12N 15/11; C12N 2310/3513; C12N 2310/50
See application file for complete search history.

(56) References Cited

U.S. PATENT DOCUMENTS

| | | |
|---|---|---|
| 10,532,109 B2 | 1/2020 | Chen et al. |
| 10,534,109 B2 | 1/2020 | Bennett |
| 2003/0104045 A1* | 6/2003 | Virtanen .................. A61P 31/12 424/94.63 |
| 2012/0165650 A1* | 6/2012 | Syud ...................... C07K 14/71 424/9.1 |
| 2022/0265838 A1 | 8/2022 | Hecht et al. |

FOREIGN PATENT DOCUMENTS

| | | | | |
|---|---|---|---|---|
| WO | WO-9010713 | * | 9/1991 | ............. A61K 37/02 |
| WO | WO-9010713 A1 | * | 9/1991 | ............. A61K 37/02 |
| WO | 2007122405 A1 | | 11/2007 | |
| WO | 2015105926 | | 7/2015 | |
| WO | WO-2017200787 A1 | * | 11/2017 | ............. A61K 38/16 |
| WO | 2021021523 A1 | | 2/2021 | |

OTHER PUBLICATIONS

Alexis et al ("HER-2 Targeted Nanoparticle-Affibody Bioconjugates for Cancer Therapy" Chem MedChem Dec. 5, 2012, pp. 1-11). (Year: 2010).*
Alavizadeh et al (Expert Opinion on drug Delivery, Nov. 24, 2015, pp. 1-36). (Year: 2015).*
Eigenbrot et al PNAS Aug. 2010 vol. 107, pp. 15039-15044). (Year: 2010).*
Govindarajan_et_al_Biomaterials_2012_Vol_33_pages_2570-2582 (Year: 2012).*
Alavizadeh, S. H., Akhtari, J., Badiee, A., Golmohammadzadeh, S., & Jaafari, M. R. (2016). Improved therapeutic activity of HER2 Affibody-targeted cisplatin liposomes in HER2-expressing breast tumor models. Expert opinion on drug delivery, 13(3), 325-336.
Alexis, F., Basto, P., Levy-Nissenbaum, E., Radovic-Moreno, A. F., Zhang, L., Pridgen, E., .& Farokhzad, O. C. (2008). HER-2-Targeted nanoparticle-affibody bioconjugates for cancer therapy. ChemMedChem: Chemistry Enabling Drug Discovery, 3(12), 1839-1843.
America Cancer Society (2016). Breast cancer survival rates. https://cancer.org/cancer/breast-cancer/understanding-a-breast-cancerdiagnosis/breast-cancer-survival-rates.html.
America Cancer Society (2016). Survival rates for prostate cancer. http://cancer.org/cancer/prostate-cancer/detection-diagnosis-staging/survivalrates.html.
Arteaga, C. L., Sliwkowski, M. X., Osborne, C. K., Perez, E. A., Puglisi, F., and Gianni, L. (2012). Treatment of HER2-positive breast cancer: current status and future perspectives. Nat. Rev. Clin. Oncol. 9, 16-32.
Berezov, A., Zhang, H. T., Greene, M. I., Murali, R. (2001). Disabling erbB receptors with rationally designed exocyclic mimetics of antibodies: structure-function analysis. J. Med. Chem. 44, 2565-74.

(Continued)

*Primary Examiner* — Catherine S Hibbert
(74) *Attorney, Agent, or Firm* — Quarles & Brady, LLP

(57) ABSTRACT

Provided herein are therapeutic agents having specificity for having inhibitory activity against cancer cells that overexpress human epidermal growth factor receptor (HER) genes, including therapeutic agents comprising one or more HER-targeting peptides, pharmaceutical compositions comprising such therapeutic agents, and methods of using such compositions to treat or prevent a cancer or other disease condition associated with HER overexpression.

18 Claims, 23 Drawing Sheets

Specification includes a Sequence Listing.

(56) References Cited

OTHER PUBLICATIONS

Cappuzzo, F., Bemis, L., and Varella-Garcia, M. (2006). HER2 mutation and response to trastuzumab therapy in non-small-cell lung cancer. N. Engl. J. Med. 354, 2619-2621.
Chaffer, C. L., Weinberg, R. A. (2011). A perspective on cancer cell metastasis. Science 331, 1559-1564.
Chen, S., and Hecht, S. M. (2008). Synthesis of pdCpAs and transfer RNAs activated with derivatives of aspartic acid and cysteine. Bioorg. Med. Chem., 16, 9023-9031.
Chen, S., Fahmi, N. E., Wang, L., Bhattacharya, C., Benkovic, S. J., and Hecht, S. M. (2013). Detection of DHFR conformational change by FRET using two fluorescent amino acids. J. Am. Chem. Soc., 135, 12924-12927.
Chen, S., Wang, L., Fahmi, N. E., Benkovic, S. J., and Hecht, S. M. (2012). Two pyrenylalanines in dihydrofolate reductase form an excimer enabling the study of protein dynamics. J. Am. Chem. Soc. 134, 18883-18885.
Chen, S., Zhang, Y., and Hecht, S. M. (2011). pThiophenylalanine-induced DNA cleavage and religation activity of a modified vaccinia topoisomerase IB. Biochemistry, 50, 9340-9351.
Dou, S., Virostko, J., Greiner, D. L., Powers A. C., and Liu, G. (2015) A feasible approach to evaluate the relative reactivity of NHS-ester activated group with primary amine-derivatized DNA analogue and non-derivatized impurity. Nucleosides Nucleotides Nucleic Acids, 34, 69-78.
Eigenbrot, C., Ultsch, M., Dubnovitsky, A., Abrahmsén, L., & Härd, T. (2010). Structural basis for high-affinity HER2 receptor binding by an engineered protein. Proceedings of the National Academy of Sciences, 107(34), 15039-15044.
Erben, C. M., Goodman, R. P., and Turberfield, A. J. (2006). Single-molecule protein encapsulation in a rigid DNA cage. Angew. Chem. Int. Ed., 45, 7414-7417.
Goodman, R. P., Heilemann, M., Doose, S., Erben, C. M., Kapanidis, A. N., and Turberfield, A. J. Nat. Nanotechnol., 2008, 3, 93-96.
Gschwind, A., Fischer, O. M., and Ullrich, A. (2004). The discovery of receptor tyrosine kinases: targets for cancer therapy. Nat. Rev. Cancer 4, 361-370.
Hellstrom, I., Goodman, G., Pullman, J., Yang, Y., and Hellstrom, K. E. (2001). Overexpression of HER-2 in ovarian carcinomas. Cancer Res. 61, 2420-2423.
Integrated DNA Technologies. Int Uni-Link Amino Modifier, Jul. 31, 2004 [online] [Retrieved Oct. 29, 2020].
International Search Report and Written Opinion for corresponding PCT/US2017/031548, dated Oct. 13, 2017.
International Search Report and Written Opinion for corresponding PCT/US2020/043099, dated Jan. 5, 2021.
Jahanzeb, M. (2008). Adjuvant trastuzumab therapy for HER2-positive breast cancer. Clin. Breast Cancer 8, 324-333.
Lambert, J. M., Chari, R.V. (2014). Ado-trastuzumab Emtansine (T-DM1): an antibody-drug conjugate (ADC) for HER2-positive breast cancer. J. Med. Chem. 57, 6949-6964.
Li, X., Kong, X., Huo, Q., Guo, H., Yan, S., Yuan, C., Moran, M. S., Shao, C., and Yang, Q. (2011). Metadherin enhances the invasiveness of breast cancer cells by inducing epithelial to mesenchymal transition. Cancer Sci. 102, 1151-1157.
Mehlen, P., and Puisieux, A. (2006). Metastasis: a question of life or death. Nat. Rev. Cancer 6, 449-458.
National Cancer Institute (2015). Types of cancer treatment. https://. cancer.gov/about-cancer/treatment/types.
Nord, K., Gunneriusson, E., Ringdahl, J., Stahl, S., Uhlen, M., Nygren, P. A. (1997). Binding proteins selected from combinatorial libraries of an β-helical bacterial receptor domain. Nat. Biotechnol. 15, 772-777.
Orlova, A., Magnusson, M., Eriksson, T. L. J., Nilsson, M., Larsson, B., Hoiden-Guthenberg, I., Widstrom, C., Carlsson, J., Tolmachev, V., Stahl, S., Nilsson, F. Y. (2006). Tumor imaging using a picomolar affinity HER2 binding affibody molecule. 66, 4339-4348.
Orlova, A., Rosik, D., Sandstrom, M., Lundqvist, H., Einarsson, L., Tolmachev, V. (2007). Evaluation of [(111/114m)In]CHX-A"-DTPA-ZHER2:342, an affibody ligand coniugate for targeting of HER2-expressing malignant tumors. Q. J. Nucl. Med. Mol. Imaging 51, 314-323.
Ozhalici-Unal, H. and Armitage, B. A. ACS nano, 2009, 3, 425-433.
Park, B.-W., Zhang, H. T., Wu, C., Berezov, A., Zhang, X., Dua, R., Wang, Q., Kao, G., O'Rourke, D. M., Greene, M. I., Murali, R. (2000). Rationally designed anti-HER2/neu peptide mimetic disables p185HER2/neu tyrosine kinases in vitro and in vivo. Nat Biotechnol 18, 194-198.
Pils, D., Pinter, A., Reibenwein, J., Alfanz, A., Horak, P., Schmid, B. C., Hefler, L., Horvat, R., Reinthaller, A., Zeillinger, R., and Krainer, M. (2007). In ovarian cancer the prognostic influence of HER2/neu is not dependent on the CXCR4/SDF-1 signalling pathway. Br. J. Cancer, 96, 485-491.
Ronnmark, J., Gronlund, H., Uhlen, M., Nygren, P. A. (2002). Human immunoglobulin A (IgA)-specific ligands from combinatorial engineering of protein A. Eur. J. Biochem. 269, 2647-2655.
Signoretti, S., Montironi, R., Manala, J., Altimari, A., Tam, C., Bubley, G., Balk, S., Thomas, G., Kaplan, I., Hlatky, L., Hahnfeldt, P., Kantoff, P., and Loda, M. (2000). Her-2-neu expression and progression toward androgen independence in human prostate cancer. J. Natl. Cancer Inst. 92, 1918-1925.
Subik, K., Lee, J. F., Baxter, L., Strzepek, T., Costello, D., Crowley, P., Xing, L., Hung, M. C., Bonfiglio, T., Hicks, D. G., and Tang, P. Breast Cancer Basic Clin. Res., 2010, 4, 35-41.
Tai, W., Mahato, R., and Cheng, K. (2010). The role of HER2 in cancer therapy and targeted drug delivery. J. Control. Release, 146, 264-275.
The Food and Drug Administration (1998). Herceptin® (trastuzumab). http://accessdata.fda.gov/drugsatfda_docs/label/2010/103792s5250lbl.pdf.
The Food and Drug Administration (2007). Tykerb (lapatinib) tablets. https://accessdata.fda.gov/drugsatfda_docs/label/2010/022059s007lbl.pdf.
The Food and Drug Administration (2012). Perjeta® (pertuzumab). http://.accessdata.fda.gov/drugsatfda_docs/label/2013/125409s051lbl.pdf.
The Food and Drug Administration (2013). Kadcyla® (ado-trastuzumab emtansine) for injection, for intravenous use. https://gene.com/download/pdf/kadcyla_prescribing.pdf.
Tran, T., Engfeldt, T., Orlova, A., Sandstrom, M., Feldwisch, J., Abrahmsen, L., Wennborg, A., Tolmachev, V., Karlstrom, A. E. (2007). (99m)Tc-maEEE-Z(HER2:342), an Affibody molecule-based tracer for the detection of HER2 expression in malignant tumors. Bioconjug. Chem. 18, 1956-1964.
Walsh et al., ACS Nano 5:5427-5432 (2011).
Wikman, M., Steffen, A. C., Gunneriusson, E., Tolmachev, V., Adams, G. P., Carlssson, J., Stahl, S. (2004). Selection and characterization of HER2/neu-binding affibody ligands. Protein Eng. Des. Sel. 17, 455-462.
Yarden, Y., and Sliwkowski, M. X. (2001). Untangling the ErbB signaling network. Nat. Rev. Mol. Cell Bio. 2, 127-137.
Zhang et al., "DNA-affibody nanoparticles for inhibiting breast cancer cells overexpressing HER2", Chem Commun (Camb). Jan. 3, 2017;53(3):573-576. doi: 10.1039/c6cc08495h.
Zhang et al., "Enhancing Antitumor Efficacy of Nucleoside Analog 5-Fluorodeoxyuridine on HER2-Overexpressing Breast Cancer by Affibody-Engineered DNA Nanoparticle," International Journal of Nanomedicine 2020:15, 885-900.

\* cited by examiner

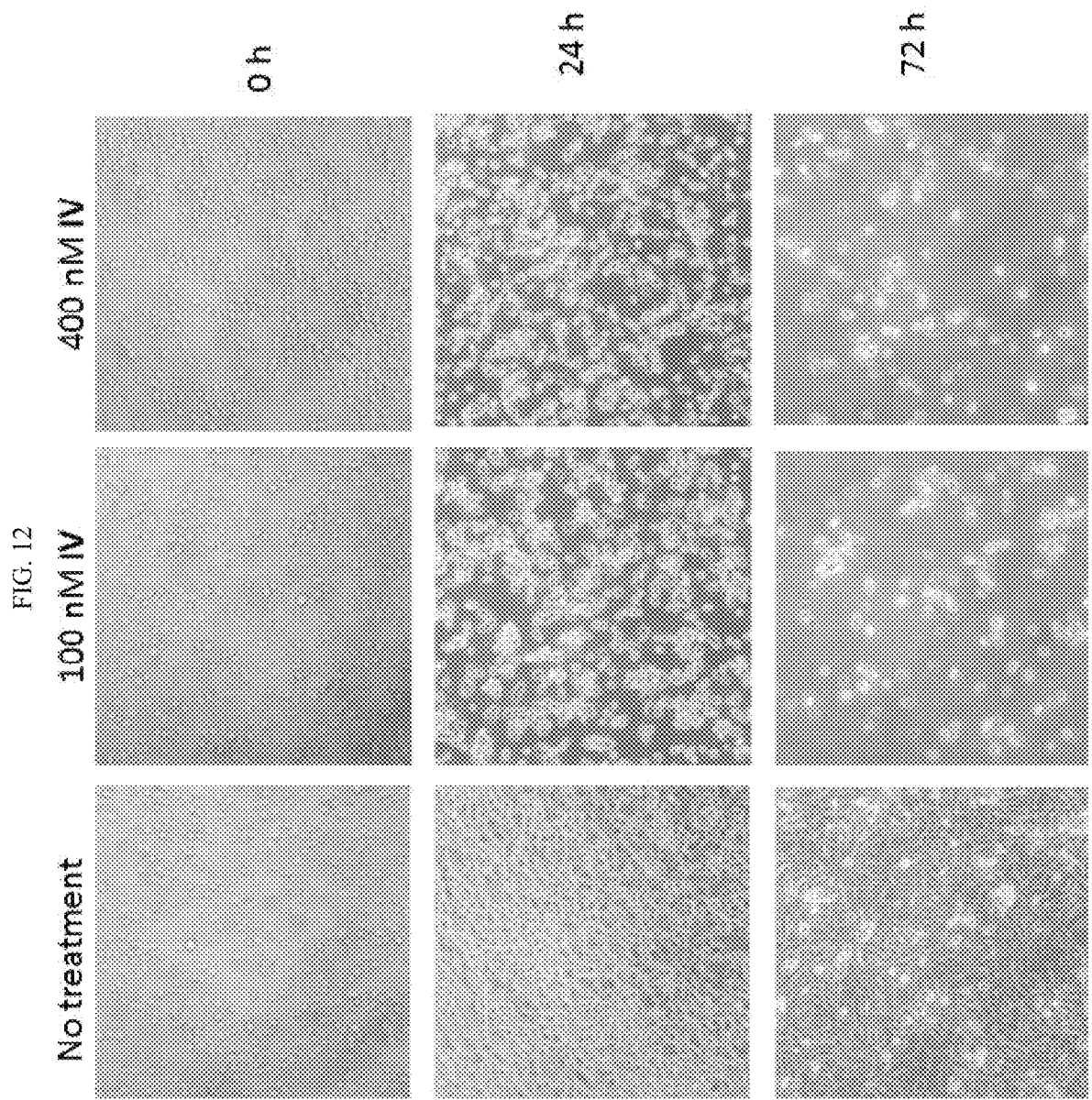

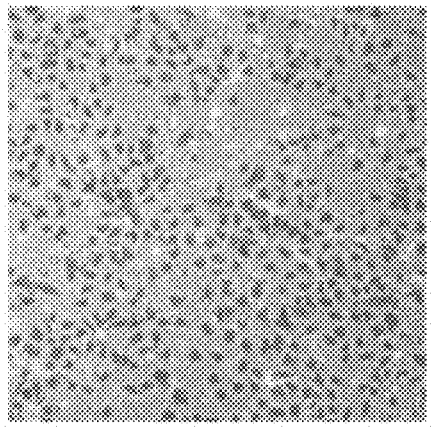
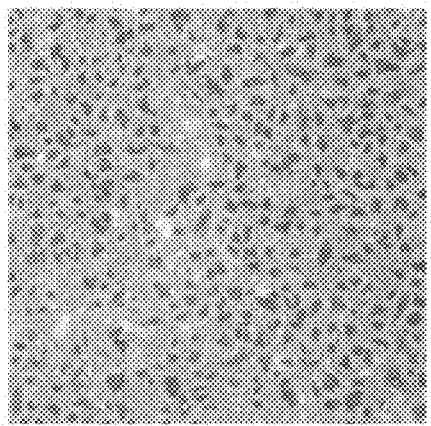
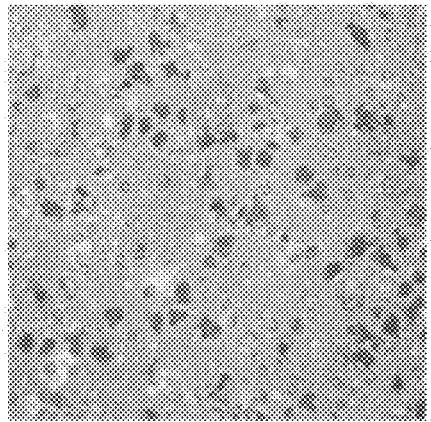
FIG. 17

SEQUENCE LISTING

```
<160> NUMBER OF SEQ ID NOS: 17

<210> SEQ ID NO 1
<211> LENGTH: 63
<212> TYPE: DNA
<213> ORGANISM: Artificial Sequence
<220> FEATURE:
<223> OTHER INFORMATION: Synthetic- amino-modified polynucleotide
<220> FEATURE:
<221> NAME/KEY: misc_feature
<222> LOCATION: (1)..(1)
<223> OTHER INFORMATION: amino modified nucleotide

<400> SEQUENCE: 1
aggcagttga gacgaacatt cctaagtctg aaatttatca cccgccatag tagacgtatc    60
acc                                                                 63

<210> SEQ ID NO 2
<211> LENGTH: 63
<212> TYPE: DNA
<213> ORGANISM: Artificial Sequence
<220> FEATURE:
<223> OTHER INFORMATION: Synthetic- amino-modified polynucleotide
```

```
<220> FEATURE:
<221> NAME/KEY: misc_feature
<222> LOCATION: (1)..(1)
<223> OTHER INFORMATION: amino modified nucleotide

<400> SEQUENCE: 2
cctcgcatga ctcaactgcc tggtgatacg aggatgggca tgctcttccc gacggtattg      60
gac                                                                   63

<210> SEQ ID NO 3
<211> LENGTH: 63
<212> TYPE: DNA
<213> ORGANISM: Artificial Sequence
<220> FEATURE:
<223> OTHER INFORMATION: Synthetic- amino-modified polynucleotide
<220> FEATURE:
<221> NAME/KEY: misc_feature
<222> LOCATION: (1)..(1)
<223> OTHER INFORMATION: amino modified nucleotide

<400> SEQUENCE: 3
cttgctacac gattcagact taggaatgtt cgacatgcga gggtccaata ccgacgatta      60
cag                                                                   63

<210> SEQ ID NO 4
<211> LENGTH: 63
<212> TYPE: DNA
<213> ORGANISM: Artificial Sequence
<220> FEATURE:
<223> OTHER INFORMATION: Synthetic- amino-modified polynucleotide
<220> FEATURE:
<221> NAME/KEY: misc_feature
<222> LOCATION: (1)..(1)
<223> OTHER INFORMATION: amino modified nucleotide

<400> SEQUENCE: 4
ggtgataaaa cgtgtagcaa gctgtaatcg acgggaagag catgcccatc cactactatg      60
gcg                                                                   63

<210> SEQ ID NO 5
<211> LENGTH: 71
<212> TYPE: PRT
<213> ORGANISM: Artificial Sequence
<220> FEATURE:
<223> OTHER INFORMATION: Synthetic- HER2 affibody

<400> SEQUENCE: 5

Met Ile His His His His His His Leu Gln Val Asp Asn Lys Phe Asn
1               5                   10                  15

Lys Glu Met Arg Asn Ala Tyr Trp Glu Ile Ala Leu Leu Pro Asn Leu
            20                  25                  30

Asn Asn Gln Gln Lys Arg Ala Phe Ile Arg Ser Leu Tyr Asp Asp Pro
        35                  40                  45

Ser Gln Ser Ala Asn Leu Leu Ala Glu Ala Lys Lys Leu Asn Asp Ala
    50                  55                  60

Gln Ala Pro Lys Val Asp Cys
65                  70

<210> SEQ ID NO 6
<211> LENGTH: 63
<212> TYPE: DNA
<213> ORGANISM: Artificial Sequence
<220> FEATURE:
<223> OTHER INFORMATION: Synthetic- amino-modified polynucleotide
```

<220> FEATURE:
<221> NAME/KEY: misc_feature
<222> LOCATION: (1)..(1)
<223> OTHER INFORMATION: amino modified nucleotide

<400> SEQUENCE: 6
caactgccta gacgaacatt cctaagtctg aaatttatca cccgccatag tagacgtatc    60
acc                                                                 63

<210> SEQ ID NO 7
<211> LENGTH: 63
<212> TYPE: DNA
<213> ORGANISM: Artificial Sequence
<220> FEATURE:
<223> OTHER INFORMATION: Synthetic- amino-modified polynucleotide
<220> FEATURE:
<221> NAME/KEY: misc_feature
<222> LOCATION: (1)..(1)
<223> OTHER INFORMATION: amino modified nucleotide

<400> SEQUENCE: 7
cctcgcatga ctaggcagtt gggtgatacg aggatgggca tgctcttccc gacggtattg    60
gac                                                                 63

<210> SEQ ID NO 8
<211> LENGTH: 63
<212> TYPE: DNA
<213> ORGANISM: Artificial Sequence
<220> FEATURE:
<223> OTHER INFORMATION: Synthetic- amino-modified polynucleotide
<220> FEATURE:
<221> NAME/KEY: misc_feature
<222> LOCATION: (1)..(1)
<223> OTHER INFORMATION: amino modified nucleotide

<400> SEQUENCE: 8
tgtagcaagc gattcagact taggaatgtt cgacatgcga gggtccaata ccgacgatta    60
cag                                                                 63

<210> SEQ ID NO 9
<211> LENGTH: 63
<212> TYPE: DNA
<213> ORGANISM: Artificial Sequence
<220> FEATURE:
<223> OTHER INFORMATION: Synthetic- amino-modified polynucleotide
<220> FEATURE:
<221> NAME/KEY: misc_feature
<222> LOCATION: (1)..(1)
<223> OTHER INFORMATION: amino modified nucleotide

<400> SEQUENCE: 9
ggtgataaaa cgcttgctac actgtaatcg acgggaagag catgcccatc cactactatg    60
gcg                                                                 63

<210> SEQ ID NO 10
<211> LENGTH: 61
<212> TYPE: PRT
<213> ORGANISM: Artificial Sequence
<220> FEATURE:
<223> OTHER INFORMATION: Synthetic- HER2 affibody

<400> SEQUENCE: 10

Val Asp Asn Lys Phe Asn Lys Glu Met Arg His Ala Tyr Trp Glu Ile
1               5                   10                  15

Val Lys Leu Pro Asn Leu Asn Pro Arg Gln Lys Arg Ala Phe Ile Arg

```
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys Val Asp Cys
    50                  55                  60

<210> SEQ ID NO 11
<211> LENGTH: 61
<212> TYPE: PRT
<213> ORGANISM: Artificial Sequence
<220> FEATURE:
<223> OTHER INFORMATION: Synthetic- HER2 affibody

<400> SEQUENCE: 11

Val Asp Asn Lys Phe Asn Lys Glu Leu Arg Gln Ala Tyr Trp Glu Ile
1               5                   10                  15

Gln Ala Leu Pro Asn Leu Asn Trp Thr Gln Ser Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys Val Asp Cys
    50                  55                  60

<210> SEQ ID NO 12
<211> LENGTH: 63
<212> TYPE: DNA
<213> ORGANISM: Artificial Sequence
<220> FEATURE:
<223> OTHER INFORMATION: Synthetic- amino-modified polynucleotide
<220> FEATURE:
<221> NAME/KEY: misc_feature
<222> LOCATION: (33)..(33)
<223> OTHER INFORMATION: N is an internal amino modifier C6 dT (iAmMC6T)

<400> SEQUENCE: 12
aggcagttga gacgaacatt cctaagtctg aantttatca cccgccatag tagacgtatc    60
acc                                                                  63

<210> SEQ ID NO 13
<211> LENGTH: 63
<212> TYPE: DNA
<213> ORGANISM: Artificial Sequence
<220> FEATURE:
<223> OTHER INFORMATION: Synthetic- amino-modified polynucleotide
<220> FEATURE:
<221> NAME/KEY: misc_feature
<222> LOCATION: (31)..(31)
<223> OTHER INFORMATION: N is an internal amino modifier C6 dT (iAmMC6T)

<400> SEQUENCE: 13
cctcgcatga ctcaactgcc tggtgatacg nggatgggca tgctcttccc gacggtattg    60
gac                                                                  63

<210> SEQ ID NO 14
<211> LENGTH: 63
<212> TYPE: DNA
<213> ORGANISM: Artificial Sequence
<220> FEATURE:
<223> OTHER INFORMATION: Synthetic- amino-modified polynucleotide
<220> FEATURE:
<221> NAME/KEY: misc_feature
<222> LOCATION: (33)..(33)
<223> OTHER INFORMATION: N is an internal amino modifier C6 dT (iAmMC6T)

<400> SEQUENCE: 14
```

```
cttgctacac gattcagact taggaatgtt cgncatgcga gggtccaata ccgacgatta    60
cag                                                                  63

<210> SEQ ID NO 15
<211> LENGTH: 63
<212> TYPE: DNA
<213> ORGANISM: Artificial Sequence
<220> FEATURE:
<223> OTHER INFORMATION: Synthetic- amino-modified polynucleotide
<220> FEATURE:
<221> NAME/KEY: misc_feature
<222> LOCATION: (31)..(31)
<223> OTHER INFORMATION: N is an internal amino modifier C6 dT (iAmMC6T)

<400> SEQUENCE: 15
ggtgataaaa cgtgtagcaa gctgtaatcg ncgggaagag catgcccatc cactactatg    60
gcg                                                                  63

<210> SEQ ID NO 16
<211> LENGTH: 30
<212> TYPE: DNA
<213> ORGANISM: Artificial Sequence
<220> FEATURE:
<223> OTHER INFORMATION: Synthetic- amino-modified polynucleotide
<220> FEATURE:
<221> NAME/KEY: misc_feature
<222> LOCATION: (1)..(1)
<223> OTHER INFORMATION: amino modified nucleotide

<400> SEQUENCE: 16
cagtctgatt gcatcgttag ctgtagatcg                                     30

<210> SEQ ID NO 17
<211> LENGTH: 30
<212> TYPE: DNA
<213> ORGANISM: Artificial Sequence
<220> FEATURE:
<223> OTHER INFORMATION: Synthetic- amino-modified polynucleotide
<220> FEATURE:
<221> NAME/KEY: misc_feature
<222> LOCATION: (1)..(1)
<223> OTHER INFORMATION: amino modified nucleotide

<400> SEQUENCE: 17
cgatctacag ctaacgatgc aatcagactg                                     30
```

DNA-AFFIBODY-DRUG NANOPARTICLES FOR INHIBITING THE METASTASIS OF CANCER CELLS OVEREXPRESSING HER2

CROSS-REFERENCE TO RELATED APPLICATIONS

This application claims priority to U.S. Provisional Application No. 62/880,272, filed Jul. 30, 2019, which is incorporated herein by reference in its entirety.

STATEMENT REGARDING FEDERALLY SPONSORED RESEARCH

Not applicable.

SEQUENCE LISTING

A Sequence Listing accompanies this application and is submitted as an ASCII text file of the sequence listing named "112624_01198_ST25.txt" which is 7,518 bytes in size and was created on Jul. 16, 2020. The sequence listing is electronically submitted via EFS-Web with the application and is incorporated herein by reference in its entirety.

BACKGROUND

Metastasis is the process by which a cancer cell locally invades the surrounding tissue, moves to the microvasculature of the blood and lymph system, migrates into distant tissues, and proliferates into a macroscopic secondary tumor. Cancer cell metastasis may occur at any stage of cancer development with more frequent incidence during last stage of cancers. All current strategies for the treatment of most kinds of cancer focus on removing the primary tumor directly (by surgery) or inhibiting the growth of the cancer (by chemotherapy and radiation). No specific strategy targets metastatic cancer cells. Therefore, the current survival rate for the metastatic cancer patients is extremely low even with optimal combination treatment via surgery, chemotherapy, and radiation. Comparatively, most cancers treated early have a high disease-free survival with optimal combination treatment because of the lower incidence rate of metastasis. For example, for stage 1 breast cancer patients, the 5-year survival rate is close 100%. For stage 2 and 3 patients, the 5-year survival rates are 93% and 72%, respectively. However, for metastatic breast cancer patients (stage 4), the 5-year survival rate is sharply reduced to 16-20%, even with currently optimal combination treatment.

Several kinds of cancer, such as breast, ovarian, gastric, prostate, lung and other cancers are associated with overexpression of human epidermal growth factor receptor 2 (HER2), which is a member of transmembrane receptor family that includes four HER receptors (HER1/EGFR, HER2, HER3 and HER4). HER receptors are essential to regulate cell proliferation and differentiation through interlinked signal transduction including Ras/Raf/MEK/MAPK and PI3K/Akt pathways. Ligand binding to the extracellular region induces the heterodimerization of HER receptors and the autophosphorylation of the HER cytoplasmic kinase domains (except for HER3 that has no kinase domain), which leads to the initiation of downstream signaling pathways. Inappropriate activation of HER receptors is associated with the initiation and development of many cancers.

As a key gene in cells, HER2 gene amplification and protein overexpression have been found in breast, ovarian, gastric, prostate, lung and other cancers. The level of HER2 overexpression ranges widely between different cancer cells and different cancer stages. The HER2 overexpression level is much higher in advanced stage of cancers. For example, overexpression of HER2 protein or amplification of its gene occurs in 28% of human ovarian cancer cases at all stages of disease; but the rate reaches almost 100% in stage III and IV. Comparably, the overall rate of HER2 overexpression among all prostate cancer cases is 25%, but the overexpression rate in late stage of prostate tumors is 78%. Overexpression of HER2 protein is associated with more frequent recurrence, spread, and significantly poorer prognosis in these kinds of cancer. The greater expression of HER2 in cancer cells than normal tissue and the accessibility of its extracellular domain make HER2 an attractive target to develop strategies for therapeutic intervention. Recently, several monoclonal antibody-based therapeutics, such as trastuzumab (Herceptin), pertuzumab, and MM-111, each of which targets the cancer cell surface antigen HER2, have been developed. Subsequently, an antibody-drug conjugate that combines the trastuzumab with a potent microtubule-disrupting agent, DM1 (T-DM1) also has been developed to increase the antibody's efficacy against HER2-positive cancers. However, a significant number of patients either do not respond or quickly relapse and exhibit resistance to existing HER2 therapies.

Small molecule drugs have been attractive agents for cancer treatment for many years because of their small size, oral availability, ability to cross membranes, and low cost. On the other hand, small molecules also have some limitations, such as low specificity and unacceptable toxicity. An antibody-drug conjugate, such as T-DM1 can specifically target HER2 overexpressing cells. However, every antibody molecule can only deliver a few molecules of a small molecule drug. In addition, the covalent bonds between antibody and drugs limit the release of the small molecule drugs. Accordingly, there remains a need for improved therapeutic compositions and therapeutic strategies for treating late stage, metastatic cancers. In particular, there remains a need for improved therapeutic compositions and methods for treating cancers, including metastatic cancers, associated with overexpression of HER2.

SUMMARY

The present disclosure overcomes the aforementioned drawbacks by providing improved therapeutic compositions and methods for treating cancers associated with overexpression of HER.

In a first embodiment, provided herein is a peptide-polynucleotide chimera comprising one or more human epidermal growth factor receptor (HER) binding peptides internally linked by a linker to a single-stranded internal amino modified polynucleotide. In some embodiments, the one or more HER binding peptides have a length of 10 amino acids to 1000 amino acids. In some embodiments, at least one of the one or more HER binding peptides is an affibody.

In some embodiments, the affibody comprises amino acid sequence SEQ ID NO:5. In some embodiments, the polynucleotide is an internal amino modified single-stranded DNA polynucleotide. In some embodiments, the internal amino modified single-stranded DNA polynucleotide has a length of 10 bases to 1000 bases. In some embodiments, the internal amino modification has the structure of iAmMC6T or iUniAmM. In some embodiments, the polynucleotide is selected from the group consisting of SEQ ID NO:12, SEQ ID NO:13, SEQ ID NO:14, and SEQ ID NO:15.

In a second aspect, provided herein is a peptide-polynucleotide tetrahedron complex comprising four peptide-polynucleotide chimeras as described herein. In some embodiments, the complex further comprises multiple molecules of a small molecule drug covalently or non-covalently bound to the peptide-polynucleotide tetrahedron complex. In some embodiments, the small molecule drug is selected from the group consisting of doxorubicin, daunorubicin, etoposide, camptothecin, cisplatin, mitomycin C, bleomycin, cyclophosphamide, 5-fluorouracil, hydroxyurea, cytosine arabinoside, and gemcitabine.

In a third aspect, provided herein is a polynucleotide tetrahedron-affibody-drug complex comprising a DNA tetrahedron having a total of six edges, four affibody molecules internally linked by a linker to internal amino modified polynucleotides of the DNA tetrahedron, and multiple molecules of a small molecule drug covalently or non-covalently bound to the DNA tetrahedron. In some embodiments, the four affibody molecules are located on four edges of the DNA tetrahedron. In some embodiments, the four affibody molecules are located on four apexes of the DNA tetrahedron. In some embodiments, the DNA tetrahedron comprises four polynucleotides selected from the group consisting of SEQ ID NO:12, SEQ ID NO:13, SEQ ID NO:14, and SEQ ID NO:15. In some embodiments, the small molecule drug is selected from the group consisting of doxorubicin, daunorubicin, etoposide, camptothecin, cisplatin, mitomycin C, bleomycin, cyclophosphamide, 5-fluorouracil, hydroxyurea, cytosine arabinoside, and gemcitabine.

In a fourth aspect, provided herein is a method of treating a cancer associated with overexpression of a human epithelial growth factor receptor (HER), the method comprising administering a therapeutically effective amount of a pharmaceutical composition comprising the peptide-polynucleotide tetrahedron complex as described herein to a subject in need thereof, whereby administration of the composition treats a cancer associated with overexpression of HER. In some embodiments, the cancer is selected from the group consisting of breast, ovarian, gastric, prostate, and lung cancer. In some embodiments, the cancer is metastatic cancer. In some embodiments, the cancer is a late-stage cancer. In some embodiments, the method of administration is by injection or by a catheter in communication with a drug delivery pump.

In a fifth aspect, provided herein is a method of suppressing gene expression in target cells of a mammal, comprising the steps of administering a peptide-polynucleotide complex described herein, whereby administration of the complex suppresses expression of HER2 in the target cells.

In a sixth aspect, provided herein is a linear peptide-polynucleotide complex comprising two peptide-polynucleotide chimeras, each peptide-polynucleotide chimera comprising one or more human epidermal growth factor receptor (HER) binding peptides, a linker, and a single-stranded polynucleotide. In some embodiments, the one or more HER binding peptides have a length of 10 amino acids to 1000 amino acids. In some embodiments, at least one of the one or more HER binding peptides is an affibody. In some embodiments, the affibody comprises amino acid sequence SEQ ID NO:5. In some embodiments, the polynucleotide is a 5' or 3' amino modified single-stranded DNA polynucleotide. In some embodiments, the single-stranded DNA polynucleotide has a length of 10 bases to 1000 bases. In some embodiments, the polynucleotide is selected from the group consisting of SEQ ID NO:16 and SEQ ID NO:17. In some embodiments, the two peptide-polynucleotide chimeras are complementary and form a double-helix structure.

In some embodiments, the linear complex further comprises multiple molecules of a small molecule drug covalently or non-covalently bound to the peptide-polynucleotide tetrahedron complex. In some embodiments, the small molecule drug is selected from the group consisting of doxorubicin, daunorubicin, etoposide, camptothecin, cisplatin, mitomycin C, bleomycin, cyclophosphamide, 5-fluorouracil, hydroxyurea, cytosine arabinoside, and gemcitabine.

In a seventh aspect, provided herein is a linear polynucleotide-affibody-drug complex comprising two DNA polynucleotides forming a double-helix structure, two affibody molecules, and multiple molecules of a small molecule drug covalently or non-covalently bound to the DNA double-helix structure. In some embodiments, the two affibody molecules are located on opposite ends of the DNA double-helix structure. In some embodiments, the DNA polynucleotides are selected from the group consisting of SEQ ID NO:16, and SEQID NO:17. In some embodiments, the small molecule drug is selected from the group consisting of doxorubicin, daunorubicin, etoposide, camptothecin, cisplatin, mitomycin C, bleomycin, cyclophosphamide, 5-fluorouracil, hydroxyurea, cytosine arabinoside, and gemcitabine.

In an eighth aspect, provided herein is a method of treating a cancer associated with overexpression of a human epithelial growth factor receptor (HER), the method comprising administering a therapeutically effective amount of a pharmaceutical composition comprising the linear peptide-polynucleotide complex as described herein to a subject in need thereof, whereby administration of the composition treats a cancer associated with overexpression of HER. In some embodiments, the cancer is selected from the group consisting of breast, ovarian, gastric, prostate, and lung cancer. In some embodiments, the cancer is metastatic cancer. In some embodiments, the cancer is a late-stage cancer. In some embodiments, the method of administration is by injection or by a catheter in communication with a drug delivery pump.

In a ninth aspect, provided herein is a method of suppressing gene expression in target cells of a mammal, comprising the steps of administering a linear peptide-polynucleotide complex described herein, whereby administration of the complex suppresses expression of HER2 in the target cells.

In a tenth aspect, provided herein is a linear polynucleotide-affibody-drug complex consisting of two DNA polynucleotides forming a double-helix structure, each DNA polynucleotide linked to an affibody molecule and multiple molecules of a small molecule drug covalently or non-covalently bound to the DNA double-helix structure. In some embodiments, the two affibody molecules are located on opposite ends of the DNA double-helix structure. In some embodiments, the DNA polynucleotides are selected from the group consisting of SEQ ID NO:16, and SEQID NO:17. In some embodiments, the small molecule drug is selected from the group consisting of doxorubicin, daunorubicin, etoposide, camptothecin, cisplatin, mitomycin C, bleomycin, cyclophosphamide, 5-fluorouracil, hydroxyurea, cytosine arabinoside, and gemcitabine.

The foregoing and other advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

(FIG. 8A) Analysis of structure nanoparticle X and its derivatives using native 5% polyacrylamide gel electrophoresis. Lane 1, DNA marker (100 bp); lane 2, 63-nt $DNA_5$; lane 3, affibody-$DNA_5$ chimera; lane 4-7, DNA tetrahedron containing 1-4 affibody molecules. (FIG. 8B) AFM micrograph of nanoparticle III.

(FIG. 11A) BT474 cells without drug treatment; (FIG. 11B) BT474 cells in the presence of 20 nM nanoparticle I; (FIG. 11C) BT474 cells in the presence of 20 nM nanoparticle II; (FIG. 11D) BT474 cells in the presence of 20 nM nanoparticle III.

FIG. 12 shows aggregation of BT474 cells induced by nanoparticle IV.

(FIG. 16A) Migrated BT474 cells without drug treatment; (FIG. 16B) Migrated BT474 cells in the presence of 20 nM nanoparticle I; (FIG. 16C) BT474 cells in the presence of 20 nM nanoparticle II; (FIG. 16D) BT474 cells in the presence of 20 nM nanoparticle III; (FIG. 16E) Calculated migration rate of BT474 cells in the presence of 20 nM nanoparticles I-III; (FIG. 16F) Calculated invasion rate of BT474 cells in the presence of 20 nM nanoparticles I-III.

FIG. 17 shows invasion of BT474 cells in the presence of 1.2 μM DOX or 100 nM nanoparticle IV. The ratio of DNA-affibody nanoparticles and DOX was 1:12 in nanoparticles IV.

DETAILED DESCRIPTION

Figure 1:
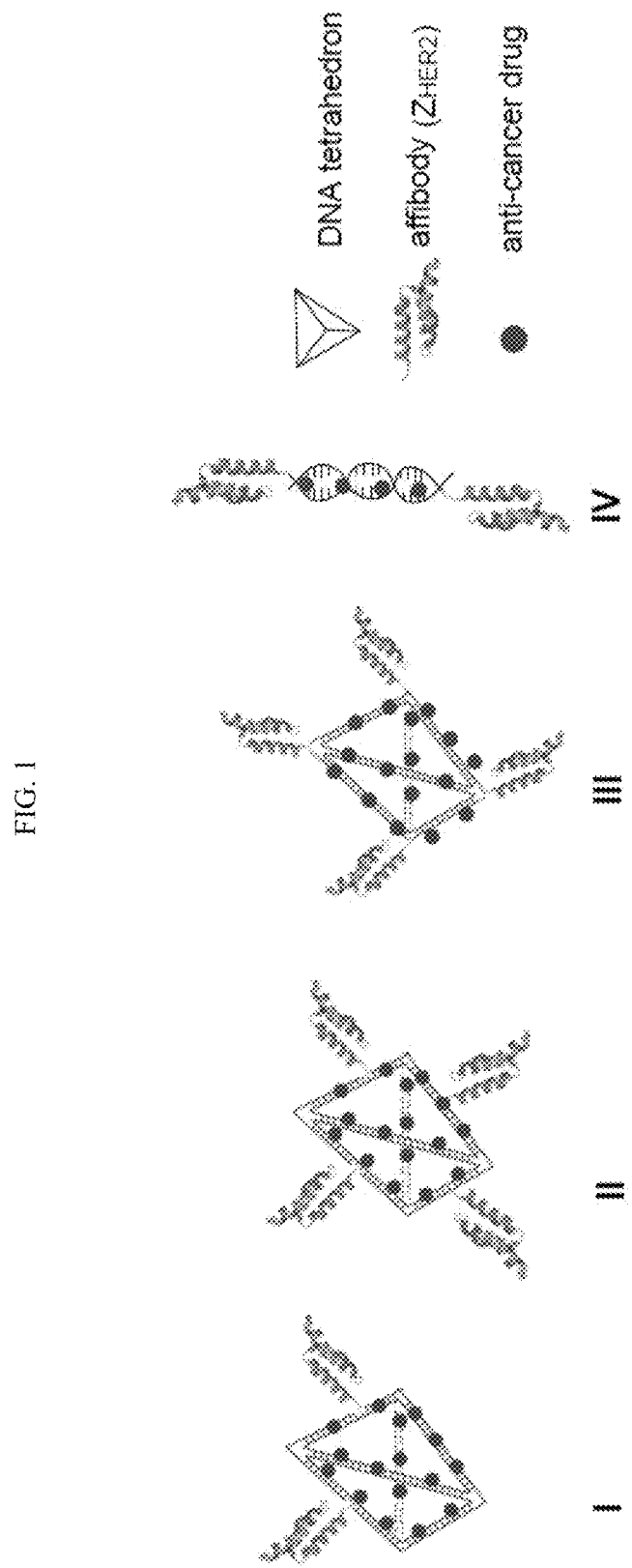
FIG. 1 shows the structures of nanoparticles I-IV.

Provided herein is a peptide-polynucleotide-drug complex and methods of treating cancers associated with overexpression of genes in the human epidermal growth factor receptor family (e.g., HER1, HER2, HER3, HER4) using compositions comprising such peptide-polynucleotide-drug complexes. The compositions and methods provided herein are based on the inventors' discovery of a nanostructure complex having inhibitory activity against HER2+ cancer cells. In particular, the inventors demonstrated that the complex specifically targets cancer cells overexpressing HER genes with higher efficiency to inhibit the cancer cells and with reduced toxicity to other cells relative to known small molecule drugs.

Accordingly, in one aspect, provided herein is a peptide-polynucleotide chimera. Referring to FIGS. 1 and 19-21, the peptide-polynucleotide chimera preferably comprises a HER2-binding peptide, a linker, and a single stranded polynucleotide (e.g., a single stranded DNA molecule). As used herein, the term "peptide-polynucleotide chimera" refers to molecules comprising peptide, polypeptide, polynucleotide, or other monomer units.

The terms "peptide," "polypeptide," and "protein" are used interchangeably to refer to a polymer of amino acid residues. The terms apply to amino acid polymers in which one or more amino acid residues is an artificial chemical analog of a corresponding naturally occurring amino acid, as well as to naturally occurring amino acid polymers. The terms polypeptide, peptide, and protein are also inclusive of modifications including, but not limited to, glycosylation, lipid attachment, sulfation, carboxylation, hydroxylation, ADP-ribosylation, and addition of other complex polysaccharides. The terms "residue" or "amino acid residue" or "amino acid" are used interchangeably to refer to an amino acid that is incorporated into a peptide, protein, or polypeptide. The amino acid may be a naturally occurring amino acid and, unless otherwise limited, may encompass non-natural analogues of natural amino acids that can function in a similar manner as naturally occurring amino acids.

The polynucleotide is preferably DNA, RNA, or a DNA or RNA derivative. The length of the polynucleotide can range of 10 to 1000 nucleotides.

In some cases, the peptide or affibody is a polypeptide of the human epidermal growth factor receptor family (e.g., HER1, HER2, HER3, HER4), or a portion thereof. In other cases, the peptide or affibody is a polypeptide that bindings to members of HER family of receptor tyrosine kinases (HER1/EGFR (epidermal growth factor receptor)/c-erbB1, HER2/c-erbB2, HER3/c-erbB3 and HER4/c-erbB4), or a portion thereof. The length of a HER-binding peptide may range from 10 to 1000 amino acids.

The peptide can be a HER2-binding peptide. In some cases, the HER2 binding peptide is an affibody, a short peptide, or a polypeptide/protein. As used herein, the term "affibody" refers to small, highly robust proteins having high affinities for specific target proteins. They can be designed and used, for example, like aptamers. Preferably, the affibody molecule has strong affinity for an extracellular domain of HER2 (e.g., an anti-HER2 affibody). In some cases, the HER2 binding peptide is a HER2 affibody comprising three alpha helix bundle domains, the amino acid sequence set forth in SEQ ID NO:5 (MIHHHHHHLQVDNKFNKEMRNAYWE-IALLPNLNNQQKRAFIRSLYDDPSQSANLLAE AKKLNDAQAPKVDC), and having a molecular weight of approximately 6 kilodaltons (kDa) and strong affinity for the HER2 receptor ($k_D$ 22 pM). Other affibody sequences that can be used include the following: VDNKFNKEMRHAY-WEIVKLPNLNPRQKRAFIRSLYDDPSQSANL-LAEAKKLNDAQAPK VDC (SEQ ID NO:10) and VDNKFNKELRQAYWEIQALPNLNWTQSRAFIRS-LYDDPSQSANLLAEAKKLNDAQAPK VDC (SEQ ID NO:11). Other suitable affibody sequences are known and available to practitioners in the art.

Suitable linkers for the peptide-polynucleotide chimeras provided herein include, without limitation, crosslinking agents having reactive moieties specific to various functional groups (e.g., sulfhydryls, amines, carbohydrates, azide, and alkyne). Exemplary linkers include, without limitation, N-[ε-maleimidocaproyloxy]succinimide ester; N-[ε-maleimidocaproyloxy]sulfosuccinimide ester; N-(β-Maleimidopropyloxy)succinimide ester; succinimidyl-4-[N-maleimidomethyl]cyclohexane-1-carboxylate; m-maleimidobenzoyl-N-hydroxysuccinimide ester.

In some embodiments, the peptide is linked to a 5' amino-modified polynucleotide using a linker as described herein. Embodiments incorporating 5' linkage of the peptide to the polynucleotide are described in more detail in U.S. Pat. No. 10,532,109, which is a national phase application corresponding to PCT Publication No. 2017/200787, each of which are incorporated herein by reference.

In some embodiments, the peptide is linked to the polynucleotide using a linker described herein linked to an internal amino modification of the polynucleotide. As used herein, "internal amino modification" refers to a polynucleotide that includes a non-naturally occurring primary amine by incorporation of an amino modified nucleotide base or incorporates the primary amine modification into the polynucleotide without adding a base such as by incorporation of an amino-modifier phosphoramidite backbone modification. The internal amino-modification in the polynucleotide may be an added amino modified base such as internal amino modifier C6 dT (iAmMC6T) or an amino-modifier phosphoramidite such as a Uni-Link™ modifier (iUniAmM) which incorporates the amino-modification without adding an additional nucleotide.

As used herein, "internal linkage" or "internally linked" refers to covalent or non-covalent attachment of the peptide or affibody to the polynucleotide at an internal amino-modified base or internal amino-modification or via formation of an imine linkage between a lysine sidechain residue and an aldehyde or ketone moiety engineered into the polynucleotide. Internal linkage is distinct from linkage of the peptide or affibody to a 5' or 3' amino-modified polynucleotide wherein the peptide or affibody is added to the end of the polynucleotide. For example, in the polynucleotide 5'-actgcta-3', a covalent or non-covalent attachment to any of the nucleotides between and including the cytosine in the $2^{nd}$ position and the thymine in the $6^{th}$ position is considered an internal linkage. Linkage at either the 5' terminal adenine or the 3' terminal adenine would be considered a terminal linkage and not an internal linkage.

As used herein, "internal modification" of "internal amino-modification" refers to modification or amino-modification of a non-5' terminal or non-3' terminal nucleotide base in a polynucleotide, the modified nucleotide base being at least 1 nucleotide away from either the 3' or 5' terminus of the polynucleotide. For example, in the polynucleotide 5'-actgcta-3' any of the nucleotides between and including the cytosine in the $2^{nd}$ position and the thymine in the $6^{th}$ position may be considered suitable for an internal modification. Modification of either the 5' terminal adenine or the 3' terminal adenine would not be considered an internal modification.

Structure of iAmMC6T:

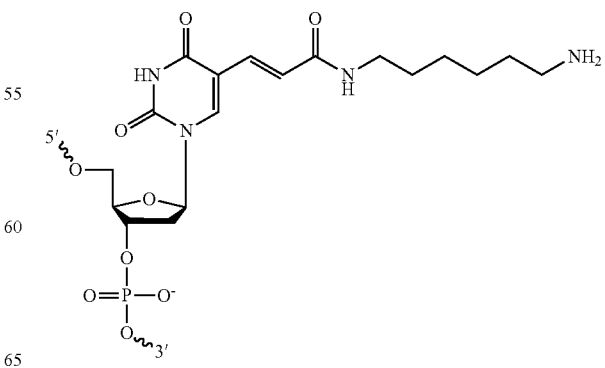

Structure of iUniAmM:

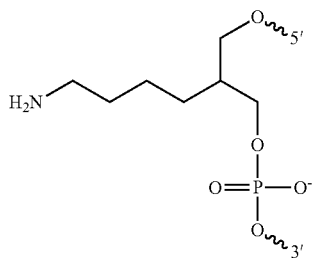

Provided herein are peptide-polynucleotide nanoparticles comprising one or more (e.g., 1, 2, 3, 4 . . . 98, 99, 100) peptide-polynucleotide chimeras as described herein. Preferably, two or more peptide-polynucleotide chimeras described herein are associated with each other to form a DNA nanostructure framework. For example, provided herein are peptide-DNA tetrahedron nanoparticles made up of one, two, or more peptide-polynucleotide chimeras as described herein and, in some cases, two polynucleotides. For drug delivery, any DNA structure should be suitable for use. Single-stranded DNA polynucleotides that can be used for the peptide-polynucleotide chimeras and/or the two additional polynucleotides can be selected from the group consisting of: $DNA_1$ (5'-$NH_2$-AGG CAG TTG AGA CGA ACA TTC CTA AGT CTG AAA TTT ATC ACC CGC CAT AGT AGA CGT ATC ACC-3' (SEQ ID NO:1)); $DNA_2$ (5'-$NH_2$-CCT CGC ATG ACT CAA CTG CCT GGT GAT ACG AGG ATG GGC ATG CTC TTC CCG ACG GTA TTG GAC-3' (SEQ ID NO:2)); $DNA_3$ (5'-$NH_2$-CTT GCT ACA CGA TTC AGA CTT AGG AAT GTT CGA CAT GCG AGG GTC CAA TAC CGA CGA TTA CAG-3' (SEQ ID NO:3)); $DNA_4$ (5'-$NH_2$-GGT GAT AAAACG TGT AGC AAG CTG TAA TCG ACG GGA AGA GCA TGC CCA TCC ACT ACT ATG GCG-3' (SEQ ID NO:4)); $DNA_9$ (5'-NH2-CAG TCT GAT TGC ATC GTT AGC TGT AGA TCG-3'(SEQ ID NO:16)); and $DNA_{10}$ (5'-NH2-CGA TCT ACA GCT AAC GAT GCA ATC AGA CTG-3' (SEQ ID NO:17)). Other polynucleotide sequences suitable for use according to the peptide-DNA tetrahedron nanoparticles described herein include: (5'-$NH_2$-CAA CTG CCT AGA CGA ACA TTC CTA AGT CTG AAA TTT ATC ACC CGC CAT AGT AGA CGT ATC ACC-3' (SEQ ID NO:6)); (5'-$NH_2$-CCT CGC ATG ACT AGG CAG TTG GGT GAT ACG AGG ATG GGC ATG CTC TTC CCG ACG GTA TTG GAC-3' (SEQ ID NO:7)); (5% $NH_2$-TGT AGC AAG CGA TTC AGA CTT AGG AAT GTT CGA CAT GCG AGG GTC CAA TAC CGA CGA TTA CAG-3' (SEQ ID NO:8)); and (5'-$NH_2$-GGT GAT AAA ACG CTT GCT ACA CTG TAA TCG ACG GGA AGA GCA TGC CCA TCC ACT ACT ATG GCG-3' (SEQ ID NO:9)).

In some embodiments, the polynucleotide is an internal amino modified polynucleotide. Suitable sequences include, but are not limited to $DNA_5$ (5'-AGG CAG TTG AGA CGA ACA TTC CTA AGT CTG AA/iAmMC6T/TTT ATC ACC CGC CAT AGT AGA CGT ATC ACC-3' (SEQ ID NO:12)); $DNA_6$ (5'-CCT CGC ATG ACT CAA CTG CCT GGT GAT ACG/iAmMC6T/GG ATG GGC ATG CTC TTC CCG ACG GTA TTG GAC-3' (SEQ ID NO:13)); $DNA_7$ (5'-CTT GCT ACA CGA TTC AGA CTT AGG AAT GTT CG/iAmMC6T/CAT GCG AGG GTC CAA TAC CGA CGA TTA CAG-3' (SEQ ID NO:14)); and $DNA_8$ (5'-GGT GAT AAAACG TGT AGC AAG CTG TAA TCG/iAmMC6T/CG GGA AGA GCA TGC CCA TCC ACT ACT ATG GCG-3' (SEQ ID NO:15)). Other suitable sequences include any of SEQ ID NOs: 1-4, 6-9, and 16-17 where in any one of the nucleotides there in has been replaced with iAmMC6T. Additionally, the polynucleotide may have the sequence of any one of SEQ ID NOs:1-4, 6-9 and 16-17 wherein the sequence additionally includes iUniAmM between any two of the nucleotides.

Figure 19:
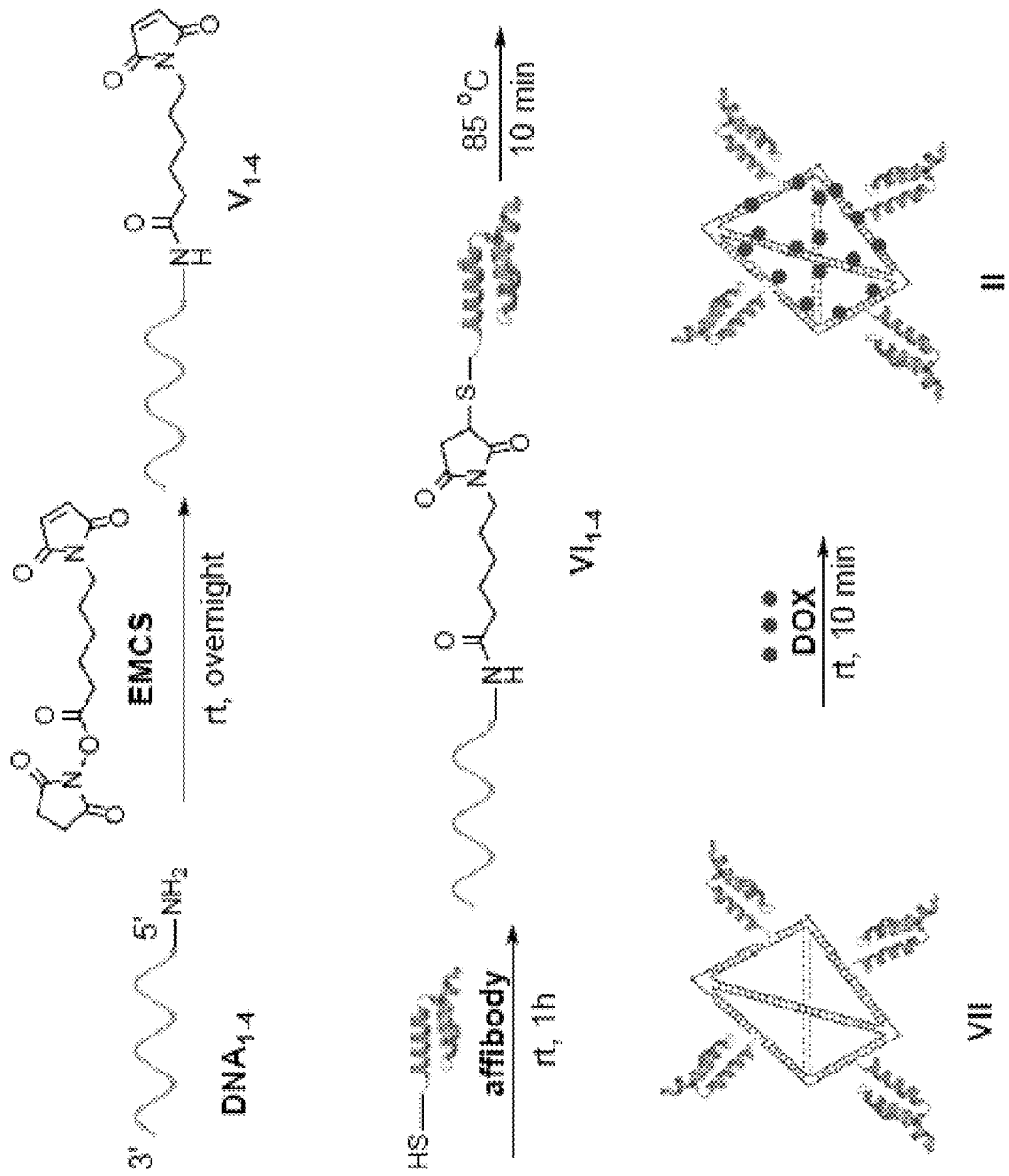
FIG. 19 shows a strategy for preparing nanoparticle II.
Figure 20:
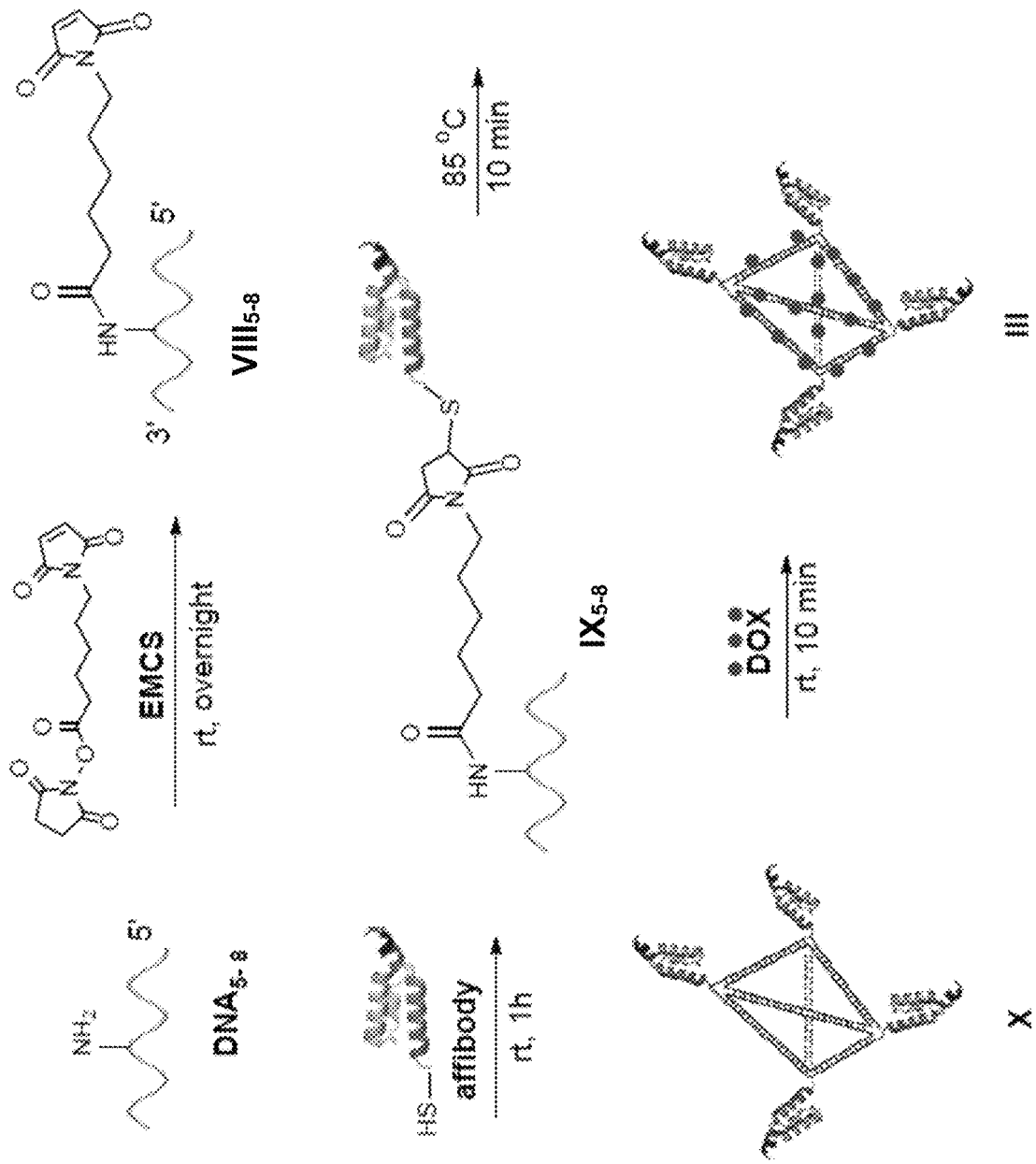
FIG. 20 shows a strategy for preparing nanoparticle III.

Referring to FIGS. 19 and 20, an exemplary protocol for synthesizing a peptide-polynucleotide tetrahedron nanoparticle comprises reacting four peptide-polynucleotide chimeras (e.g., affibody-polynucleotide chimeras) in the presence of 10 mM Tris.HCl, pH 8.0, containing 10 mM of $MgCl_2$, and incubating the reaction mixture at about 60° C. to about 90° C. Generally, DNA tetrahedron structures are described by Walsh et al., ACS Nano 5:5427-5432 (2011).

In another aspect, provided herein is a peptide-DNA tetrahedron-drug nanoparticle (II, III, and IV) comprising a peptide-DNA tetrahedron nanoparticle or linear peptide-DNA complex as described herein and a plurality of molecules of a small molecule drug. The plurality of molecules can be bound to the nanoparticle through non-covalent binding or covalent binding. By appending a HER2-binding peptide (e.g., an anti-HER2 affibody) to a tetrahedral DNA nanostructure, one may obtain a functional, multiform DNA nanostructure useful for as carriers for delivery of drugs or other compounds or biomolecules. For example, peptide polynucleotide tetrahedron nanostructures provide a high capacity vehicle for binding and delivering small molecule anti-cancer drugs to target cells. The peptide-polynucleotide tetrahedron-drug complex as shown in FIGS. 1, 19, 20 and 21 demonstrate greater binding capacity for HER2 overexpressing cancer cells as compared to small molecule drugs not associated with such a nanostructure. In addition, the peptide-polynucleotide tetrahedron-drug complex shows greater efficacy for inhibiting HER2 overexpressing cancer cells as well as decreased toxicity for normal cells. Accordingly, the peptide-polynucleotide tetrahedron-drug complexes described herein provide a novel class of anti-cancer drugs.

Small molecule drugs for inclusion in a peptide-polynucleotide tetrahedron-drug complex described herein include, without limitation, doxorubicin (DOX), daunorubicin, etoposide, camptothecin, cisplatin, mitomycin C, bleomycin, cyclophosphamide, 5-fluorouracil, hydroxyurea, cytosine arabinoside, and gemcitabine. For example, DOX is a broad spectrum, FDA-approved drug anticancer agent that binds reversibly to DNA. The target of the peptide-tetrahedron-drug nanoparticle (III) includes all HER2 positive (HER+) cancer cells including, without limitation, breast, ovarian, gastric, prostate, lung, and other cancers.

The peptide-polynucleotide chimeras and peptide-polynucleotide tetrahedron-drug nanoparticles described herein provide a highly efficient approach to specifically delivering small molecule drugs to HER2 overexpressed cancer cells. When a plurality of molecules of a small molecule drug are bound to a nanoparticle as described herein via non-covalent binding, the plurality of molecules can dissociate from the nanoparticle upon entry or contact to the target cancer cell. Each vehicle nanostructure has capacity to delivery tens to hundreds of molecules of an anti-cancer drug. Without being bound by any particular theory or mode of action, it is believed that an anti-HER2 peptide or affibody attached to a DNA tetrahedron will also bind a small molecule anticancer agent such as doxorubicin to target and bind HER2 expressing cancer cells and, consequently, block metastasis and induce apoptosis of targeted HER2+ cancer cells.

In some cases, it may be advantageous to attach one or more of the above-identified small molecule drugs to the peptide-DNA tetrahedron using, for example, a degradable linker. Linkers suitable for the nanoparticles described herein include, without limitation, DNA, RNA, peptides, polysaccharides, esters, amides, and disulfide bonds.

In another aspect, provided herein is a polynucleotide tetrahedron-affibody-drug complex, where the complex comprises a DNA tetrahedron having a total of six edges, four affibody molecules, and multiple molecules of a small molecule drug covalently or non-covalently bound to the DNA tetrahedron. Referring to FIG. 1, the four affibody molecules can be located on four edges of the DNA tetrahedron, forming an asymmetric structure. Alternatively, the four affibody molecules can be located on four apexes of the DNA tetrahedron, forming a symmetric structure. DNA tetrahedrons can comprise four DNA polynucleotides, which can be selected from the group consisting of SEQ ID NOs:1-17. The DNA polynucleotides can include a 5' amino modification, a 3' amino modification, or an internal amino modification. In some embodiments, the small molecule drug can be doxorubicin. Other small molecule drugs include, without limitation, daunorubicin, etoposide, camptothecin, cisplatin, mitomycin C, bleomycin, cyclophosphamide, 5-fluorouracil, hydroxyurea, cytosine arabinoside, gemcitabine, and the like.

Figure 21:
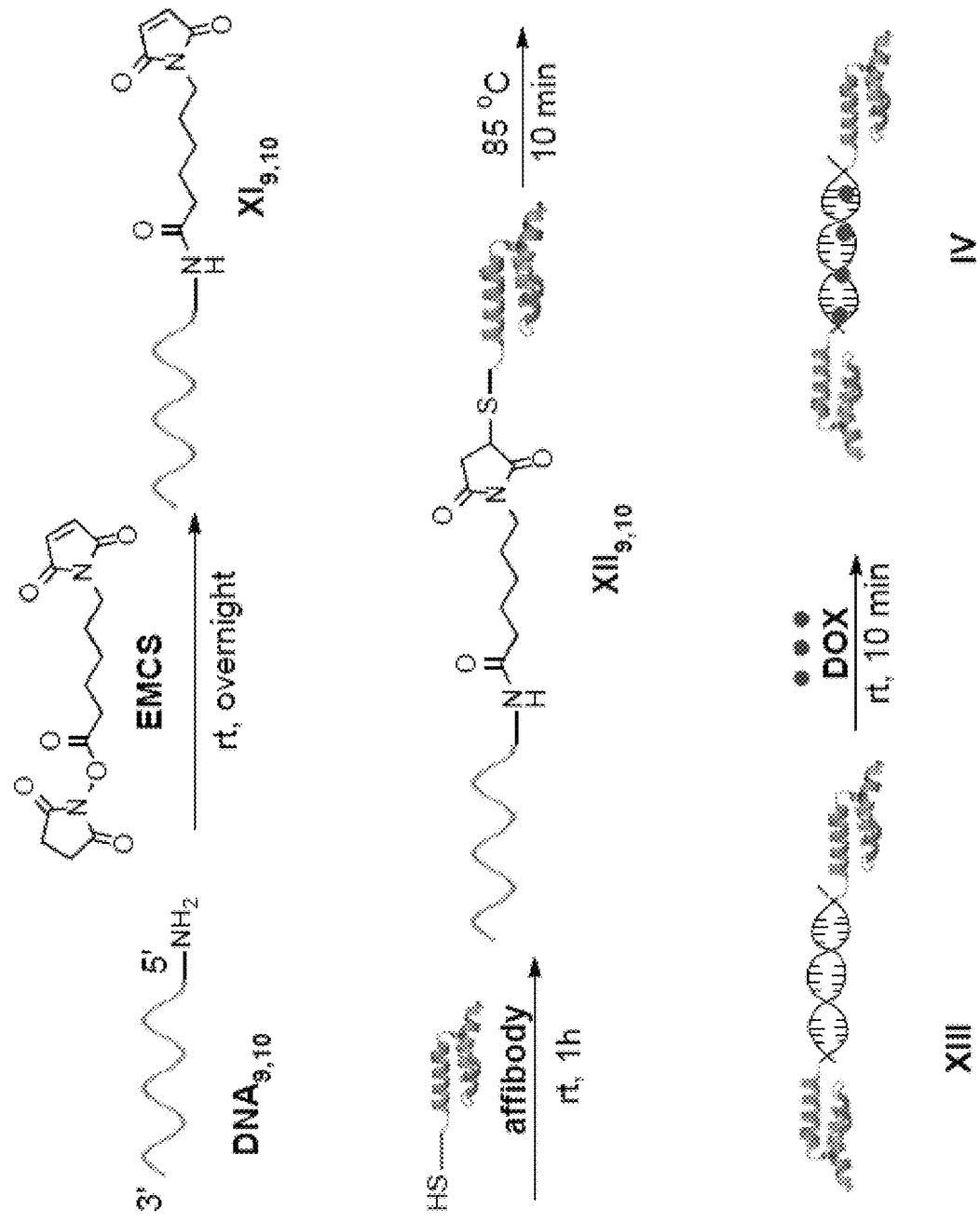
FIG. 21 shows a strategy for preparing nanoparticle IV.

In another aspect, the nanoparticles can be other structures, such as linear type, Y-type, or polygon structures, or any other geometric structure recognized as suitable by persons of ordinary skill in the art in view of the teachings herein. In some embodiments, the polynucleotide-affibody-drug complex has a linear structure as depicted in FIG. 1 and FIG. 21. The linear DNA structure includes two affibody molecules, two polynucleotides and at least one molecule of a small molecule drug covalently or non-covalently bound to the linear DNA structure. The two affibody molecules can be located one opposite ends of the linear DNA structure. Alternatively, the two affibody molecules can be internally linked to the polynucleotide and oriented on opposite sides of the linear DNA structure. The DNA polynucleotides of the linear DNA structure can be, but are not limited to, the sequences of SEQ ID NOs:16 and 17. The DNA polynucleotides can include a 5' amino modification, a 3' amino modification, or an internal amino modification. In some embodiments, the small molecule drug can be doxorubicin. Other small molecule drugs include, without limitation, daunorubicin, etoposide, camptothecin, cisplatin, mitomycin C, bleomycin, cyclophosphamide, 5-fluorouracil, hydroxyurea, cytosine arabinoside, gemcitabine, and the like.

In a further aspect, provided herein are methods for treating cancers associated with overexpression of HER2 or other HER molecules. As used herein, the terms "treating," "treat," and "treatment" refer to the management and care of a patient for the purpose of combating the disease, condition, or disorder. The terms embrace both preventative, i.e., prophylactic, and palliative treatments. In some cases, the term "treated" refers to any beneficial effect on progression of a disease or condition. Beneficial effects can include reversing, alleviating, inhibiting the progress of, preventing, or reducing the likelihood of the disease or condition to which the term applies or one or more symptoms or manifestations of such a disease or condition. Where the disease or condition is a tumor, cancer, or cancer-associated condition, treating can refer to the management and care of a patient for the purpose of combating cancer, and can include reversing, alleviating, inhibiting the progress of, preventing, reducing the size of, or reducing the likelihood of, or lessening the severity of any aspect of the cancer or cancer-associated condition (e.g., metastasis, tumor growth). A therapeutic beneficial effect on the health and well-being of a patient includes, but it not limited to: (1) curing the cancer; (2) slowing the progress of the cancer; (3) causing the tumor to regress; or (4) alleviating one or more symptoms of the cancer. As used herein, the terms "preventing" and "prevent" refer not only to a complete prevention of a certain disease or condition, but also to partially or substantially attenuating, reducing the risk of, or delaying the development or recurrence of the disease or condition to which the term applies.

In some cases, the cancer is a late-stage cancer. As used herein, the term "late-stage cancer" refers a clinical stage III or stage IV cancer as determined by a qualitative or quantitative assessment of the level of advancement of a cancer. Criteria used to determine the stage of a cancer include, without limitation, the size of the tumor, amount of nodes where the cancer has spread, and the extent of metastases (e.g., localized or distant), and will be known to those skilled in the art. It will be understood by those skilled in the art that criteria for determining the stage of a cancer may vary depending on the type of cancer.

In some cases the methods provided herein are directed to treating or preventing a tumor cancer in a subject by administering a therapeutically effective amount of a compound provided herein. A "therapeutically effective amount" of a compound refers to an amount of the compound that alleviates, in whole or in part, symptoms associated with a disorder or disease, or slows or halts further progression or worsening of those symptoms, or prevents or provides prophylaxis for the disease or disorder in a subject at risk for developing the disease or disorder. A therapeutically effective dose relates to the amount of a compound that is sufficient to improve the symptoms, for example a treatment, healing, prevention or improvement of such conditions. In exemplary embodiments, a therapeutically effective amount or dose is an amount such that free antibody is present in the blood. For dosage determinations, it can be advantageous to assess toxicity and therapeutic efficacy of a compound in cell cultures or in experimental animals. For example, the $LD_{50}$ (i.e., the dose lethal to 50% of the population) and $ED_{50}$ (i.e., the dose therapeutically effective in 50% of the population) can be determined. From these calculations, dosage ranges for use in humans can be formulated. Dosage ranges can vary depending on factors such as mode of administration. A therapeutically effective amount of a pharmaceutical composition provided herein can range from about 0.001 to 100 mg of nanoparticle per kg body weight of the subject (e.g., about 0.01 to 100 mg/kg body weight; about 0.1 to 40 mg/kg body weight; about 1 to 20 mg/kg body weight).

A "subject" or "patient" is a member of any animal species, preferably a mammalian species, optionally a human. The subject can be an apparently healthy individual, an individual suffering from a disease, or an individual being treated for a disease.

The terms "delivering," "deliver," "administering," and "administers" can be used interchangeably to indicate the introduction of any agent (e.g., a therapeutic agent) into the body of a patient in need thereof to treat a disease or condition, and can further mean the introduction of any agent into the body for any purpose. The terms encompass any route of introducing or delivering to a subject a compound to perform its intended function. A composition comprising a peptide-tetrahedron-drug nanoparticle as provided herein can be delivered or administered to a subject by any method that achieves the intended purpose or is deemed appropriate by those of skill in the art. For example, a composition of the present invention can be administered as a pharmaceutical, and may be administered systemically or locally via oral or parenteral administration. As used herein, the term "administration" includes oral and parenteral administration. Oral administration includes, for example, administration of oral agents. Such oral agents include, for example, granules, powders, tablets, capsules, solutions, emulsions, and suspensions. Parenteral administration includes, for example, administration of injections. Such injections include, for example, subcutaneous injections, intramuscular injections, and intraperitoneal injection. In some cases, intravenous injections such as drip infusions, intramuscular injections, intraperitoneal injections, subcutaneous injections, suppositories, enemas, oral enteric tablets, or the like can be selected. In some cases, the method of administration is by injection or by a catheter in communication with a drug delivery device. "Drug delivery device" encompasses any and all devices that administers a therapeutic agent to a patient and includes infusion pumps, implanted or percutaneous vascular access ports, direct delivery catheter systems, local drug-release devices or any other type of medical device that can be adapted to deliver a therapeutic to a patient.

Appropriate modes of administration can be determined based on the physical location of a tumor or tumors in the subject's body. In exemplary embodiments, a composition comprising a peptide-tetrahedron-drug nanoparticle as provided herein is administered to a subject having a diagnosis of lung cancer or a pre-cancerous lesion, where the composition is administered orally or intravenously. Alternatively, a composition comprising a peptide-tetrahedron-drug nanoparticle can be administered locally to an intended area of treatment. For example, a composition comprising a peptide-tetrahedron-drug nanoparticle can be administered by local application during surgery.

Compositions can be administered to a subject in need thereof in dosage unit form where each discrete dosage unit contains a predetermined quantity of an active ingredient or compound that was calculated to elicit a desirable therapeutic effect when administered with, in some cases, a pharmaceutically acceptable buffer or carrier. The terms "pharmaceutically acceptable buffer" and "pharmaceutically acceptable carrier" are meant to encompass any buffer or carrier, which does not interfere with the effectiveness of the biological activity of the active ingredient and that is not toxic to the host to which it is administered.

Treatment or prevention according to a method provided herein can occur before, during, or after the subject is treated by surgery, radiation, and/or chemotherapy. In some cases, treatment according to a method provided herein prior to chemo- or radiotherapy may improve the outcome of the conventional therapy. In an exemplary embodiment, a compound as provided herein is administered to a subject concurrently with one or more other treatments or preventative measures such as radiotherapy, chemotherapy, or surgery.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Chemicals and Apparatus—All chemicals were purchased and used without further purification. The DNAs were purchased from Integrated DNA Technologies, Inc. (Skokie, IL). Nε-malemidocaproyloxysuccinimide ester was obtained from AstaTech Inc. (Bristol, PA). Doxorubicin hydrochloride was purchased from Oakwood Products Inc. (Columbia, SC). Trastuzmab was obtained from BioVision Inc. (Milpitas, CA). Ni-NTA agarose was obtained from QIAGEN Inc. (Valencia, CA). Sephadex G-25, imidazole, sodium chloride, sodium acetate, polyacrylamide, trizma base, acetic acid, ethylenediaminetetraacetic acid (EDTA), magnesium chloride and ethanol were obtained from Sigma-Aldrich Chemicals (St. Louis, MO). Amicon® ultra centrifugal filters were purchased from Merck Millipore Ltd. (Darmstadt, Germany). Gibco® RPMI 1640 medium, trypsin, 3-(4,5-dimethylthiazol-2-yl)-2,5-diphenyl-2H-tetrazolium bromide (MTT) and dimethylsulfoxide (DMSO) were purchased from Sigma-Aldrich (St. Louis, MO, USA). Antibotic-antimycotic (100 X), fetal bovine serum (FBS), and DAPI were purchased from Thermo Fisher Scientific (Waltham, MA, USA). Transwell® chambers and matrigel matrix were purchased from Corning Incorporated. (Kennebunk, ME).

UV spectral measurements were made using an Agilent Technologies Cary 60 UV/Vis spectrometer. DNA gels were imaged using a VWR UV-transilluminator-20 gel imager. The nanoparticles were scanned using a Bruker Dimension FastScan atomic force microscopy.

Preparation of DNA-affibody—The sequences of the single-strand DNAs for preparing DNA tetrahedron were listed in Table 1. The sequence of the affibody used in this study was MIHHHHHHLQVDNKFNKEMRNAYWE-IALLPNLNNQQKRAFIRSLYDDPSQSANLLAEA KKLNDAQAPKVDC (SEQ ID NO:5). The affibody was expressed in E. coli cells and purified using a Ni-NTA column.

Each single-strand DNA (200 μg, 10.3 nmol) was dissolved in 160 μL of phosphate-buffered saline (PBS, 10 mM $PO_4^{3-}$, 137 mM NaCl, and 2.7 mM KCl) and treated with 40 μL of 10 mM Nε-malemidocaproyloxysuccinimide ester (EMCS) in dimethyl sulfoxide. The reaction mixture was incubated at room temperature for overnight and stopped by the addition of 20 μL of 3M NaOAc. After the addition of 600 μL of ethanol and incubation at 4° C. for 30 min, the reaction mixture was centrifuged at 15000 g for 30 min. After washing with 70% ethanol, the DNA was dissolved in 50 μL of PBS buffer and treated with 300 μg (38.1 nmol) of affibody in 300 μL of PBS buffer. After incubation at room temperature for 1 h, the reaction mixture was stopped by the addition of 35 μL of 3M NaOAc. After the addition of 1000 μL of ethanol and incubation at 4° C. for 30 min, the reaction mixture was centrifuged at 15000 g for 30 min. After washing with 70% ethanol, the DNA-affibody was dissolved in 200 μL of 50 mM Tris.HCl, pH 8.0, containing 300 mM NaCl.

The DNA-affibody in the solution was purified on a Ni-NTA chromatography column. The crude product solution (200 μL) was loaded on a column containing 300 μL of Ni-NTA resin. Then the column was washed five times with 300 μL of 50 mM Tris.HCl, pH 8.0, containing 300 mM NaCl and 5 mM imidazole. Finally, the Ni-NTA column was eluted three times with 300 μL of 50 mM Tris.HCl, pH 8.0, containing 30 mM NaCl and 150 mM imidazole. The elute from the previous step was further purified on a column containing 200 μL DEAE-Sepharose. The column was eluted with 200 μL PBS buffer containing 0.2-0.9 M NaCl. Each elution was added 20 μL of 3M NaOAc and 600 μL of ethanol. After incubation at 4° C. for 30 min, the mixture was centrifuged at 15000 g for 30 min. After washing with 70% ethanol, the product was dissolved in 200 μL of $H_2O$. The product was analyzed by 8% denaturing polyacrylamide gel electrophoresis (PAGE). The gel was run at 110 V for 1 h, and stained with ethidium bromide.

Preparation of DNA tetrahedron-affibody nanoparticle—$DNA_1$-affibody (10.0 nmol), $DNA_2$-affibody (10.0 nmol), $DNA_3$-affibody (10.0 nmol), and $DNA_4$-affibody (10.0 nmol) were added 8 mL of 10 mM Tris.HCl, pH 8.0, containing 10 mM $MgCl_2$. The reaction mixture was incubated at 85° C. for 10 min then cooled to room temperature over a period of 30 min. The obtained DNA tetrahedron-affibody nanoparticle was analyzed by 5% native polyacrylamide gel electrophoresis (PAGE). The gel was run at 110 V for 1 h, and stained with ethidium bromide.

Preparation of DNA tetrahedron-affibody-doxorubicin nanoparticle—The DNA tetrahedron-affibody nanoparticle prepared in the previous step was concentrated using Amicon® ultra centrifugal filters (MW cutoff 50 kDa). The concentrated DNA tetrahedron-affibody nanoparticle (5 μM) in 100 μL of 10 mM Tris.HCl, pH 8.0, containing 10 mM $MgCl_2$ was treated with 5 μL of 10 mM doxorubicin and incubated at room temperature for 10 min. Excess DOX was removed on a Sephadex G-25 column.

Atomic force microscopy (AFM) characterization—For DNA tetrahedron-affibody nanoparticle imaging, 10-μL samples (10 nM) were deposited onto a freshly peeled mica surface for 2 min. Next, 10 μL of 100 mM $NiCl_2$ solution was added to assist adsorption. Finally, 55 μL of TAE/Mg2+ buffer (40 mM Tris, 20 mM acetic acid, 2 mM EDTA, 12 mM $MgCl_2$, pH 8.0) was added onto the mica and another 55 μL, of TAE/$Mg^{2+}$ buffer was added on the atomic force microscope (AFM) tip. The samples were imaged in ScanAsyst in Fluid mode (with a ScanAsyst-liquid+tip) with Dimension FastScan AFM (Bruker).

Biological activity of nanoparticles—BT474 breast cancer cells (ATCC® HTB-20, overexpression of HER2) and MDA-MB-231 breast cancer cells (ATCC® HTB-26, low expression of HER2 receptor) were cultured at 37° C. in a 5% $CO_2$ atmosphere and grown in Gibco® RPMI 1640 medium supplemented with 10% fetal bovine serum (FBS) and 1% antibotic-antimycotic mix antibiotic supplement before use.

Exponentially growing BT474 cells and MDA-MB-231 cells were harvested and plated in 96-well plates at a concentration of 2×104 cells/well for BT474 cells and 5×104 cells/well for MDA-MB231 cells. After incubation at 37° C. for 24 h, the cells were treated with DOX, DNA tetrahedron-affibody-DOX nanoparticles I-IV at different concentrations for an additional 72 hours.

Then 20 μL it of MTT (5 mg/mL) was added to each well and the plates were incubated at 37° C. for 4 h. The supernatant was discarded, and 100 μL of DMSO was added to each well. The absorbance was recorded at 490 nm after 15 min. Inhibition of cell growth was calculated using the following formula: Inhibition of cell growth (%)= $(OD_{negative\ control}-OD_{treatment})\times 100\%/(OD_{negative\ control}-OD_{background})$. Data are reported as the mean of three independent experiments, each run in quintuplicate.

Migration assay of BT474 and MDA-MB-231 Cells— The 24-well transwell chambers (8 μm pore size) were balanced with 200 μL of RPMI 1640 medium (serum free) for 2 h at 37° C. in a 5% $CO_2$ atmosphere. After removing the medium, $3.6\times10^4$ cells in 180 μL of RPMI 1640 medium (serum free) were added to each chamber followed by adding 20 μL of nanoparticles (200 nM) or 20 μL Tris-HCl (10 mM, pH 8.0). To the lower compartment of each well was added 800 μL of RPMI 1640 medium containing 10% serum.

After incubation for 48 h, cells were fixed with 4% formaldehyde followed by 100% methanol and stained with 0.2% crystal violet. The non-migrated cells on the upper surface of the chamber were removed with a cotton swab and the migrated cells on the lower surface of the chamber were imaged using a light microscope.

Invasion assay of BT474 and MDA-MB-231 Cells—The 24-well transwell chambers (8 μm pore size) were coated with 100 μL of matrigel matrix (150 mg/mL) for 2 h at 37° C. in 5% $CO_2$ atmosphere. After removing the uncoated solution, $3.6\times10^4$ cells in 180 μL of RPMI 1640 medium (serum free) were added to each chamber followed by adding 20 μL of nanoparticles (200 nM) or 20 μL Tris-HCl (10 mM, pH 8.0). To the lower compartment of each well was added 800 μL of RPMI 1640 medium containing 10% serum. After incubation for 48 h, cells were fixed with 4% formaldehyde followed by 100% methanol and stained with 0.2% crystal violet. The non-migrated cells on the upper surface of the chamber were removed with a cotton swab and the migrated cells on the lower surface of the chamber were imaged using a light microscope.

Fluorescence microscopy—BT474 cells (ATCC® HTB-20, overexpression of HER2) were seeded in 8-well chambered cover glasses (Ibidi). Live cells were washed with 1×PBS buffer on ice and imaged for two minutes after addition of each agent (1 μM DOX, 0.02 μM III, 1×CellBrite red cytoplasmic membrane dye, or 1×Hoechst 33342 fluorescent stain). Control cells were treated with 1×PBS buffer. Samples were imaged with a Nikon C2 scanning confocal on a Nikon Ti microscope, using a 40×plan apo, water immersion lens, with numerical aperture of 1.2. Excitation lasers of 405 nm, 561 nm, and 640 nm were paired with DAPI, TRITC, and Cy5 channel detectors, respectively. Images were post-processed using the Nikon Elements software and Adobe Photoshop. DOX intensity values are normalized to DNA content and presented as the ratio of total signal in the red channel relative total intensity in the blue (DAPI) channel.

Western Blot Analysis—BT474 cells (50,000 cells/mL) were seeded in a 6-well cell culture plate and incubated in 1 mL of Gibco® RPMI 1640 medium supplemented with 10% fetal bovine serum (FBS) and 1% antibiotic-antimycotic mix antibiotic supplement at 37° C. for 24 h in a 5% $CO_2$ atmosphere. After treatment with 1 μM DOX, 0.02 μM III and a positive control antibody (1 μM Herceptin) for 1 h, the culture medium was removed. The cells were washed with 1 mL 1×PBS buffer, and treated with 150 μL Cellstripper® non-enzymatic cell dissociation solution. After centrifugation at 500×g for 3 min, the cell pellets were washed with 150 μL 1×PBS buffer and treated with 60 μL, of 1×RIPA lysis buffer containing protease and phosphatase inhibitor cocktail (Sigma-Aldrich). After three cycle of freeze, thaw and sonication following by centrifugation at 15,000×g for 2 min at 4° C., the clear supernatant was collected.

Total protein concentration was measured using a BCA kit (Thermo Fisher Scientific). NuPAGE LDS Sample Buffer (4×) and NuPAGE Reducing Agent (10×) was added to the lysate which was denatured at 70° C. for 5 min. Equal amounts of lysates (25 μg) were loaded on a 4%-12% SDS-polyacrylamide Bis-Tris gels (Invitrogen) according to the manufacturer's recommendations and then proteins were transferred to nitrocellulose membranes. After blocking with 5% dry milk in TBST buffer (1×Tris-Buffered Saline, 0.1% Tween® 20) for 1 h at room temperature to inhibit non-specific binding, the nitrocellulose membranes were incubated with primary HER2/ErbB2 rabbit Ab (10 μg/mL, Cell Signaling Technology), phosphor-HER2/ErbB2 (Y1221/1222) rabbit mAb (10 μg/mL, Cell Signaling Technology), or anti-α-tubulin mouse mAb (2 μg/mL, Calbiochem), respectively overnight at 4° C. Following three 5-min washes with TBST, the nitrocellulose membranes were incubated with horseradish peroxidase-linked anti-rabbit IgG (5 μg/mL, Cell Signaling Technology) or horseradish peroxidase-linked anti-mouse IgG, respectively at room temperature for 1 h. The blots were washed three times for 5 min with TBST, rinsed with deionized $H_2O$, and treated with SuperSignal West Pico Chemiluminescent Substrate (Pierce Biotechnology) at room temperature for 2 min, and the signals were scanned using an Azure Imaging System.

Results:

As the simplest DNA three-dimensional structure, a DNA tetrahedron has provided a rigid platform for biological applications. We coupled two affibody molecules to a DNA tetrahedron nanoparticle to mimic the structure of a monoclonal antibody, composed of two Fab and one Fc regions. (See U.S. Pat. No. 10,534,109, which issued from a national phase application corresponding to PCT Publication No. 2017/200787, each of which is incorporated herein by reference). This DNA tetrahedron-affibody-doxorubicin (DOX) nanoparticle (I, FIG. 1) has high specificity and efficacy, and low toxicity; it may form the basis for a strategy to treat HER2 overexpressing breast cancers. However, all these agents lack the ability to block the metastasis of breast cancers. Here we report two mutifunctional DNA tetrahedron-affibody-drug nanoparticles containing four affibody molecules covalently coupled to four edges/apexes of a DNA tetrahedron, of which the latter binds tens of anticancer drug molecules (II and III, FIG. 1). In addition, one linear double-stranded DNA-affibody-doxorubicin nanoparticle containing two affibody molecules covalently coupled to two ends of the DNA (IV) was also prepared.

Figure 2:
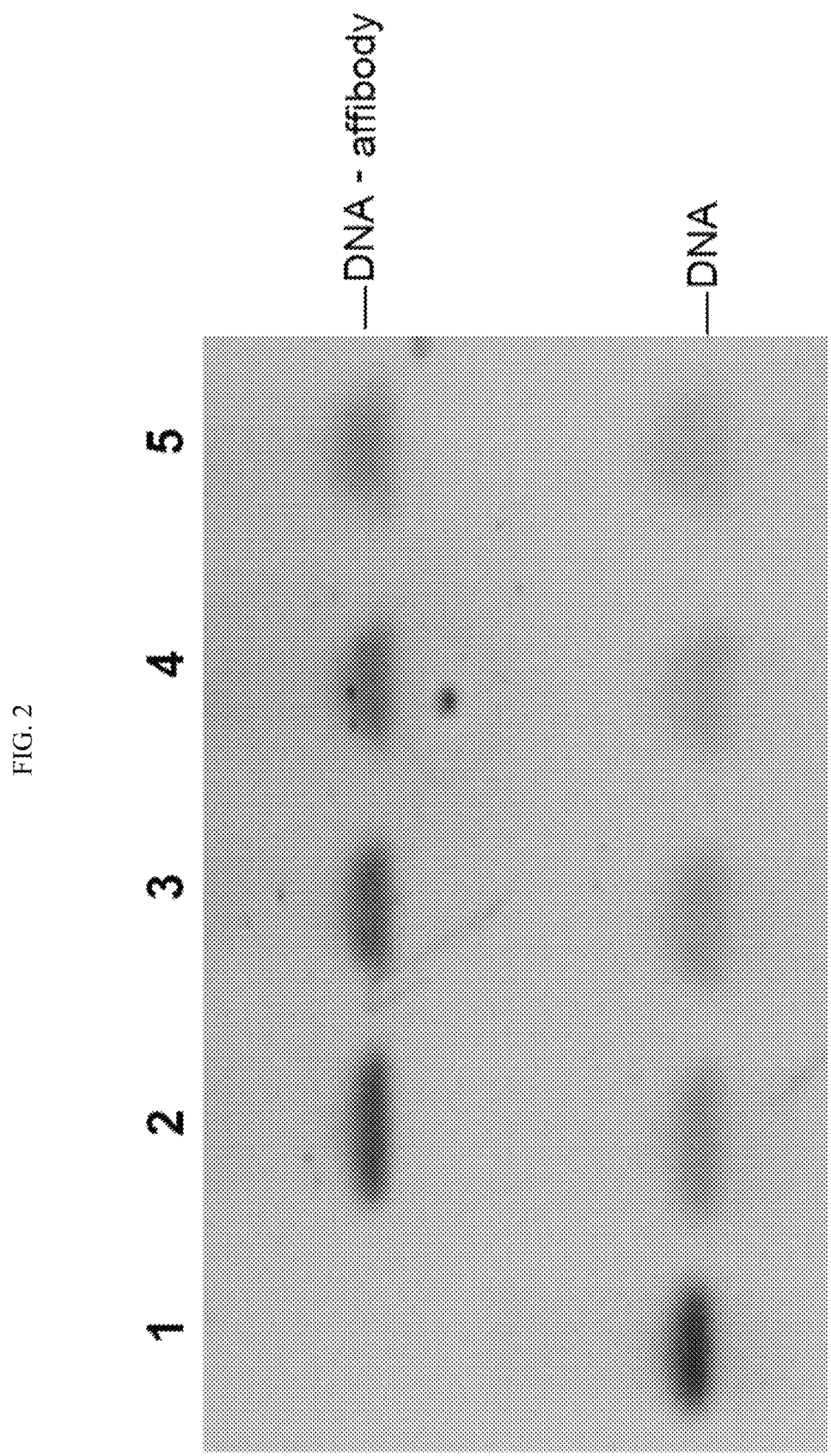
FIG. 2 shows the coupling reaction of the affibody with $N^\varepsilon$-malemidocaproyl-oxysuccinimide ester (EMCS)-linked DNA. The results were analyzed on a 15% denaturing polyacrylamide gel (7 M urea) followed by ethidium bromide staining. Lane 1, $DNA_1$; lane 2, $EMCS-DNA_1$; lane 3, $EMCS-DNA_2$; lane 4, $EMCS-DNA_3$; lane 5, $EMCS-DNA_4$.
Figure 3:
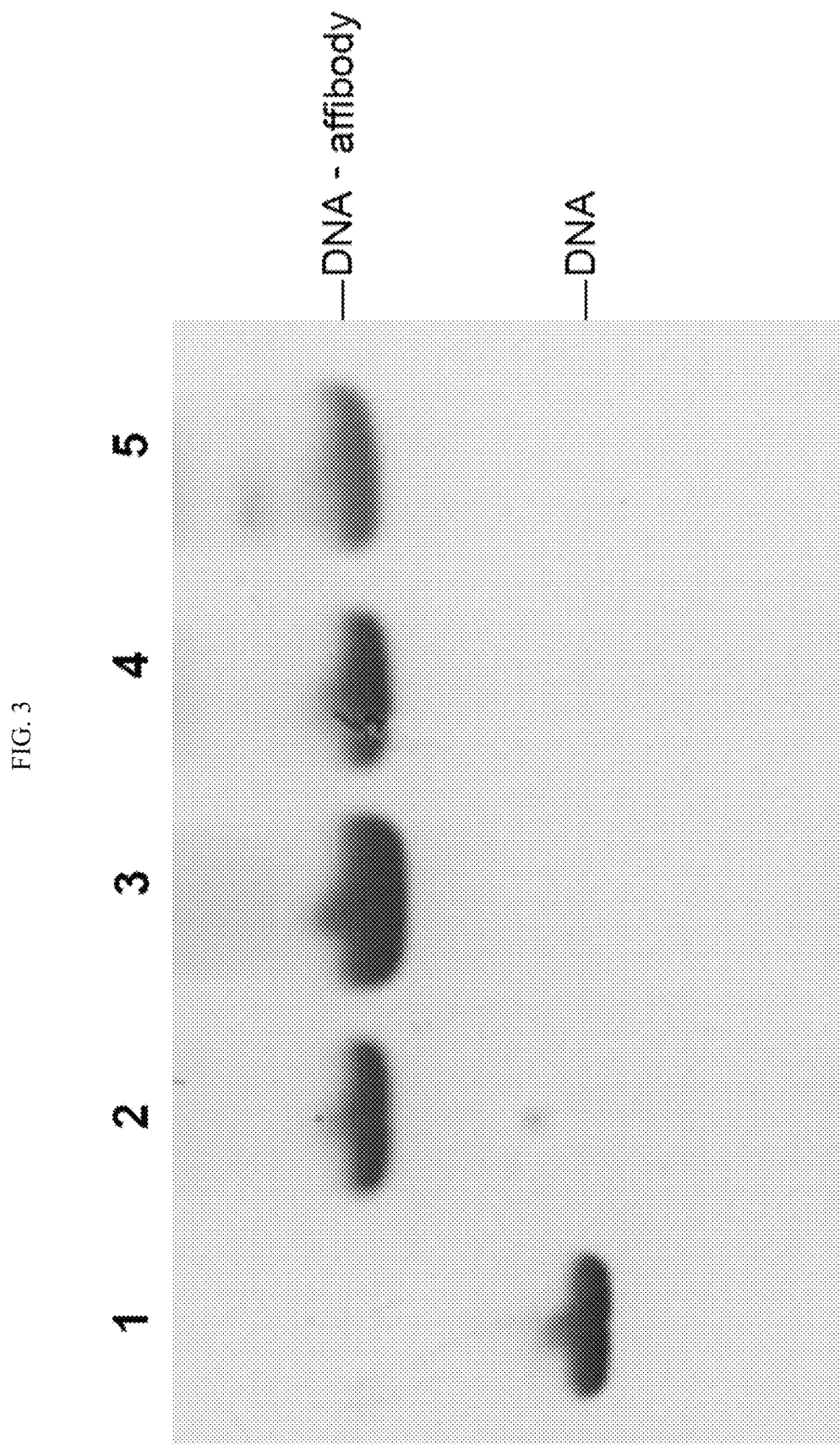
FIG. 3 shows purification of DNA-affibody using a Ni-NTA followed by DEAE-Sepharose CL-6B column. The results were analyzed on a 15% denaturing polyacrylamide gel (7 M urea) followed by ethidium bromide staining. Lane 1, 1 μg DNA1; lane 2, DNA1-affibody; lane 3, DNA2-affibody; lane 4, DNA3-affibody; lane 5, DNA4-affibody.
Figure 4:
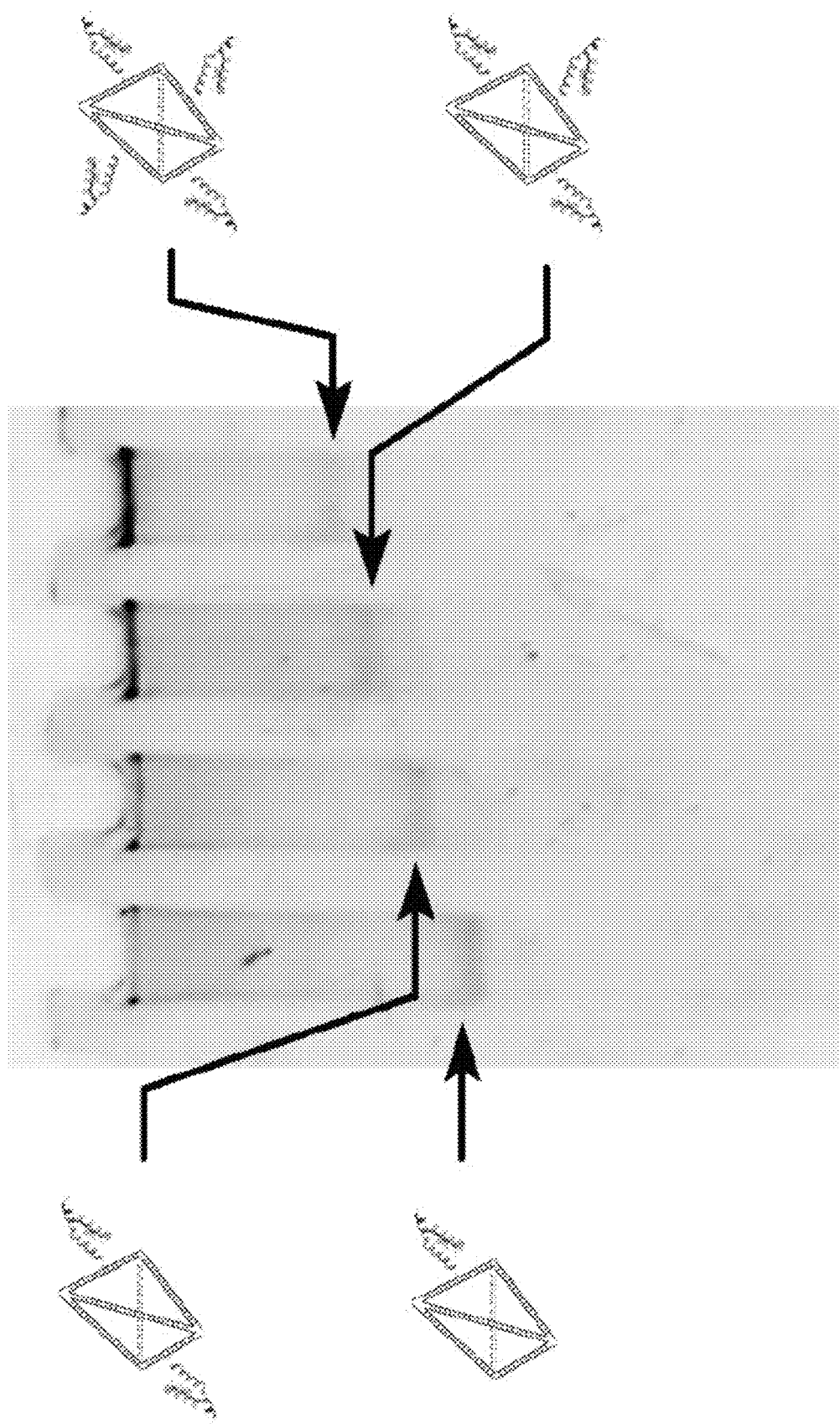
FIG. 4 shows analysis of the structure of nanoparticle VII. Analysis of nanoparticle VII structure and its analogs using native 5% polyacrylamide gel electrophoresis.
Figure 5:
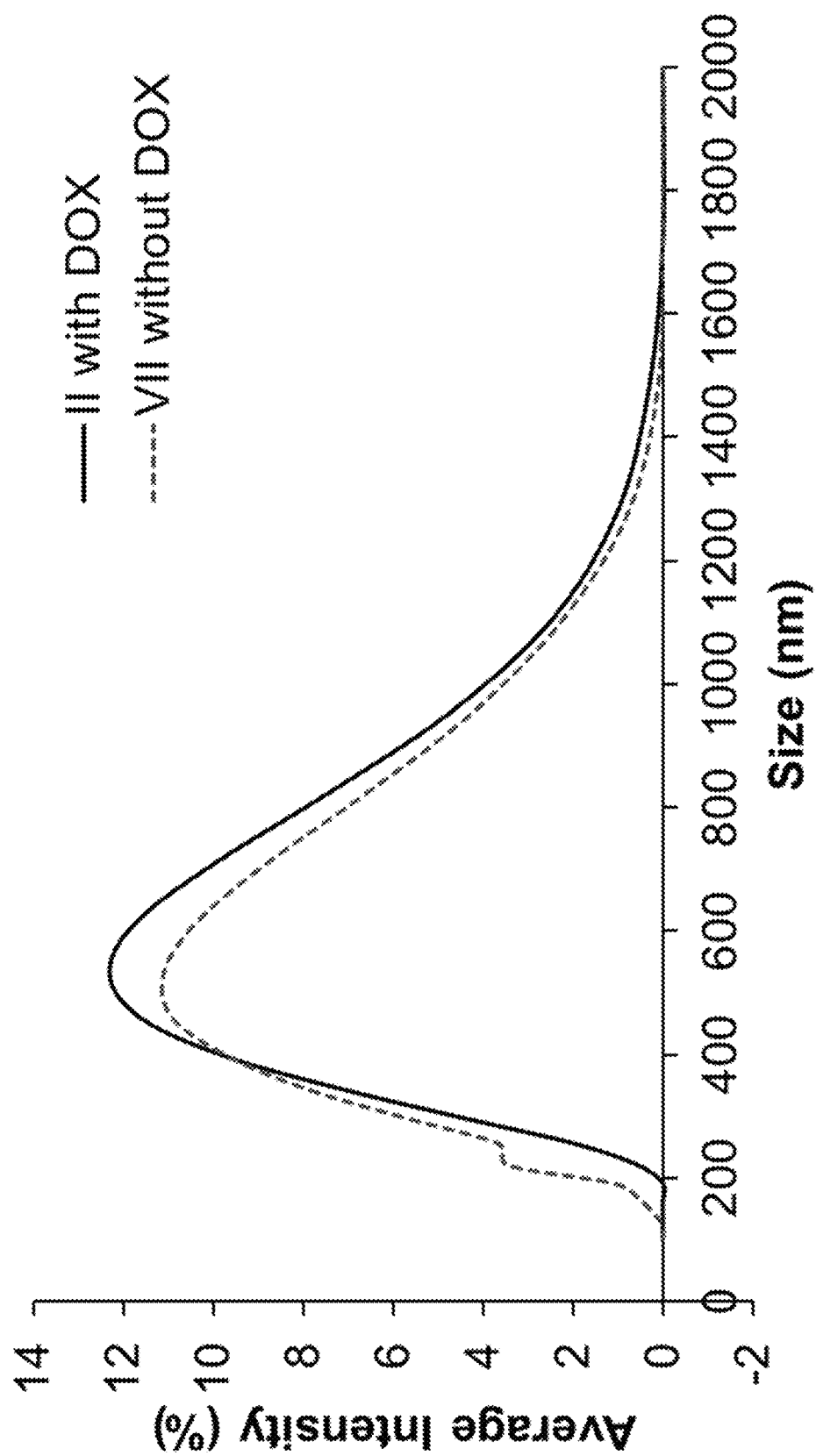
FIG. 5 shows hydrated particle size of nanoparticles VII (without DOX) and II (containing DOX).

The antibody-like nanoparticle I has been prepared following the reported procedure as a control. It was prepared by coupling two affibody molecules to two 63-nt single-strand DNAs at the 5'-end and annealing them with another two uncoupled 63-nt single-strand DNAs. The nanoparticle II and III were designed as two antibodies fused together tail-by-tail. Each structure can bind to two adjacent cells separately and crosslink them together. The nanoparticle II was prepared by coupling four affibody molecules to four 63-nt single-strand DNAs ($DNA_{1-4}$) at the 5'-end (see scheme in FIG. 19 and data in FIG. 2; the DNA sequences are listed in Table 1), for which the procedure was same as for the nanoparticle I. After purification and quantification (FIG. 3), these four DNA-affibody molecules were heated at 85° C. for 5 min and cooled to room temperature during 30 min to form the nanoparticle VII, which contained four affibody molecules at four edges of a DNA tetrahedron (FIG. 4). It was reported that each DNA tetrahedron of a comparable size binds about 50 DOX molecules. The obtained DNA tetrahedron-affibody nanoparticle was treated with a 50-fold molar excess of doxorubicin to generate nanoparticle II, whose hydrated particle size is same as nanoparticle VII (FIG. 5).

TABLE 1

DNA sequences for preparing nanoparticles II-IV

| Name | Sequence | SEQ ID NO: |
|---|---|---|
| $DNA_1$ | 5'-$NH_2$-AGG CAG TTG AGA CGA ACA TTC CTA AGT CTG AAA TTT ATC ACC CGC CAT AGT AGA CGT ATC ACC-3' | 1 |
| $DNA_2$ | 5'-$NH_2$-CCT CGC ATG ACT CAA CTG CCT GGT GAT ACG AGG ATG GGC ATG CTC TTC CCG ACG GTA TTG GAC-3' | 2 |
| $DNA_3$ | 5'-$NH_2$-CTT GCT ACA CGA TTC AGA CTT AGG AAT GTT CGA CAT GCG AGG GTC AAT ACG ACG ATTA CAG-3' | 3 |
| $DNA_4$ | 5'-$NH_2$-GGT GAT AAAACG TGT AGC AAG CTG TAA TCG ACG GGA AGA GCA TGC CCA TCC ACT ACT ATG GCG-3' | 4 |
| $DNA_5$ | 5'-AGG CAG TTG AGA CGA ACA TTC CTA AGT CTG AA/iAmMC6T/ TTT ATC ACC CGC CAT AGT AGA CGT ATC ACC-3' | 12 |
| $DNA_6$ | 5'-CCT CGC ATG ACT CAA CTG CCT GGT GAT ACG /iAmMC6T/GG ATG GGC ATG CTC TTC CCG ACG GTA TTG GAC-3' | 13 |
| $DNA_7$ | 5'-CTT GCT ACA CGA TTC AGA CTT AGG AAT GTT CG/iAmMC6T/ CAT GCG AGG GTC AAT ACG ACG ATTA CAG-3' | 14 |
| $DNA_8$ | 5'-GGT GAT AAAACG TGT AGC AAG CTG TAA TCG /iAmMC6T/CG GGA AGA GCA TGC CCA TCC ACT ACT ATG GCG-3' | 15 |

TABLE 1-continued

DNA sequences for preparing nanoparticles II-IV

| Name | Sequence | SEQ ID NO: |
|---|---|---|
| $DNA_9$ | 5'-$NH_2$-CAG TCT GAT TGC ATC GTT AGC TGT AGA TCG-3' | 16 |
| $DNA_{10}$ | 5'-$NH_2$-CGA TCT ACA GCT AAC GAT GCA ATC AGA CTG-3' | 17 |

Figure 6:
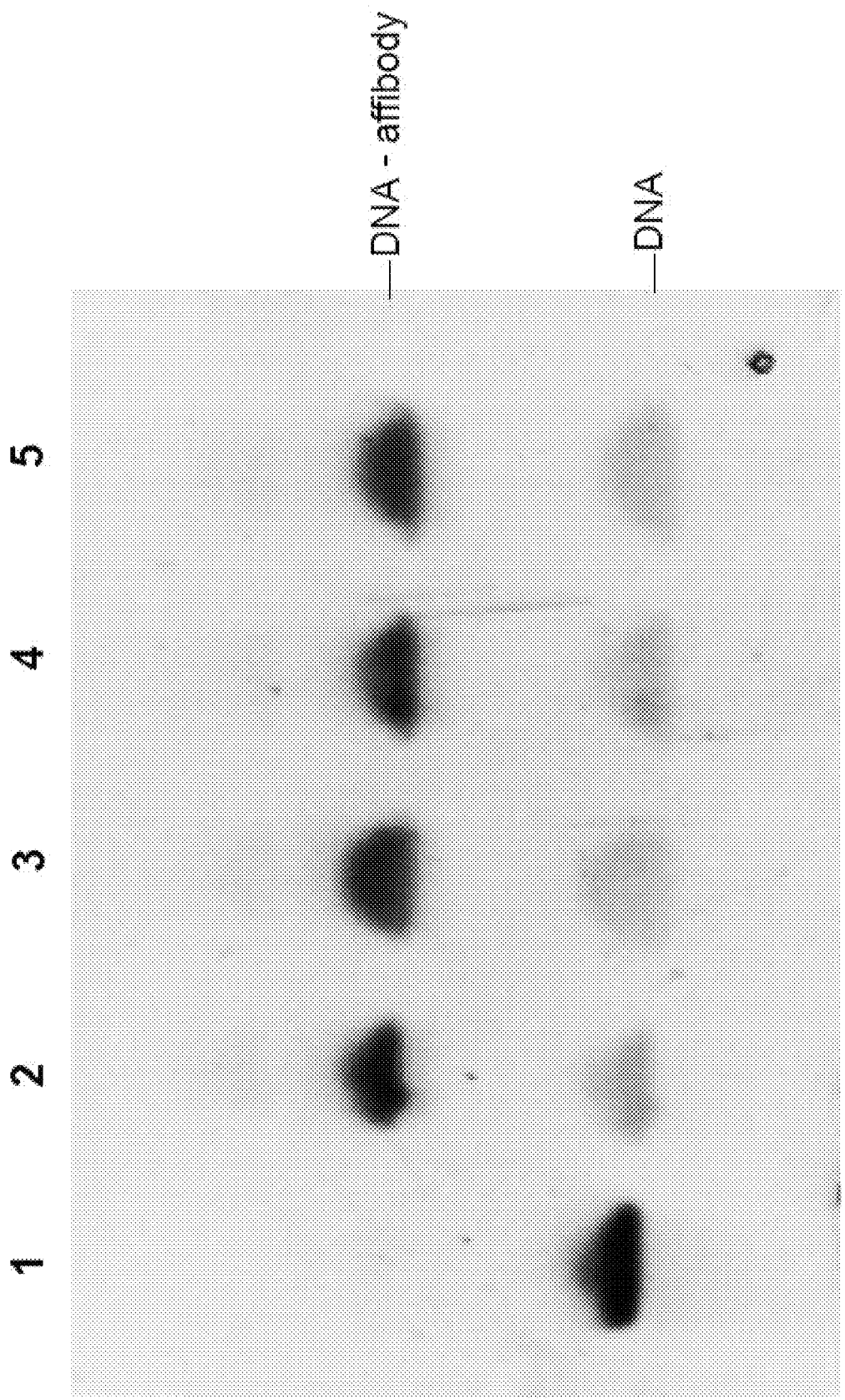
FIG. 6 shows coupling reaction of the affibody with EMCS-linked DNA. The results were analyzed on a 15% denaturing polyacrylamide gel (7 M urea) followed by ethidium bromide staining. Lane 1, $DNA_5$; lane 2, $EMCS-DNA_5$; lane 3, $EMCS-DNA_6$; lane 4, $EMCS-DNA_7$; lane 5, $EMCS-DNA_8$.
Figure 7:
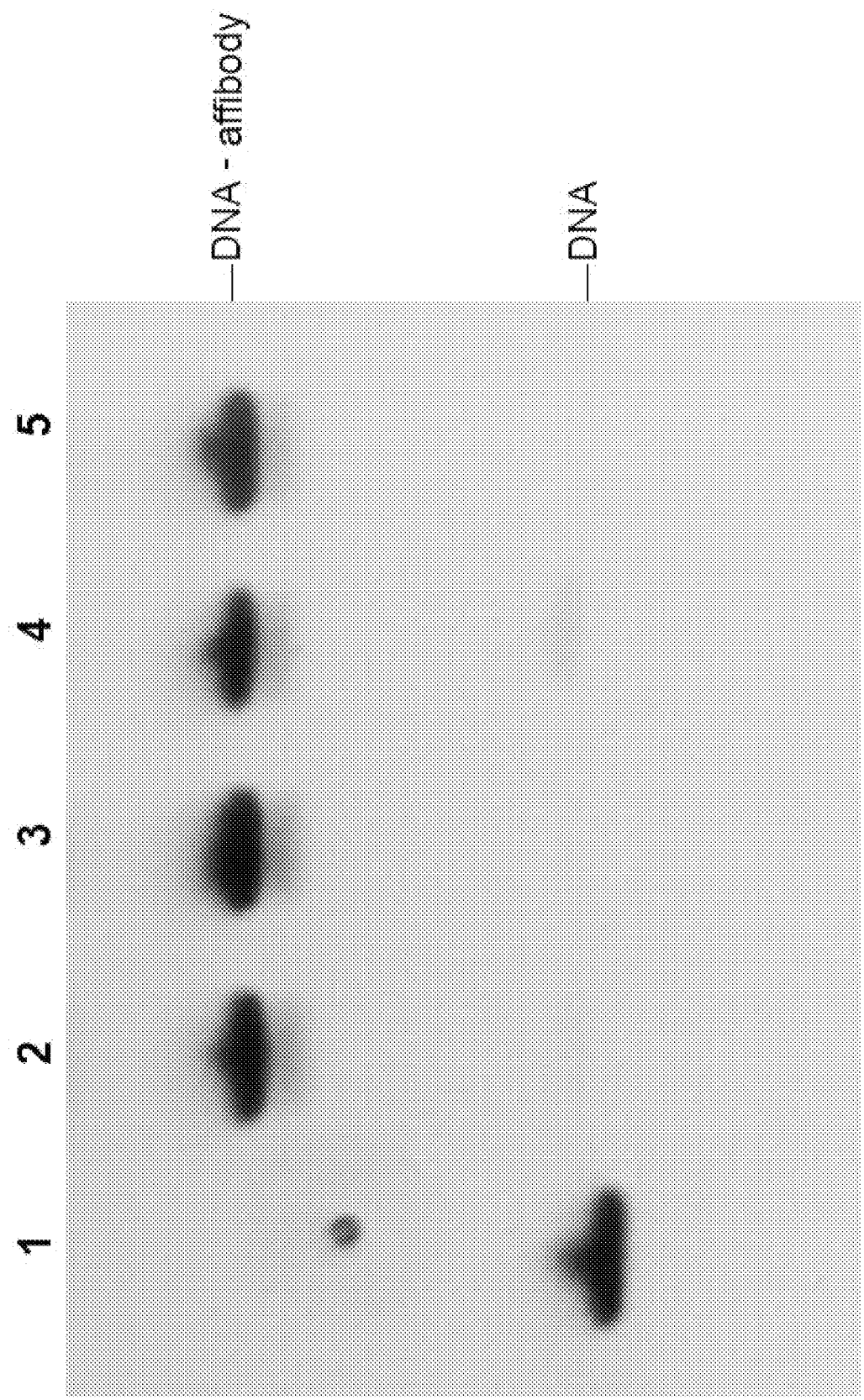
FIG. 7 shows purification of DNA-affibody using a Ni-NTA followed by DEAE-Sepharose CL-6B column. The results were analyzed on a 15% denaturing polyacrylamide gel (7 M urea) followed by ethidium bromide staining. Lane 1, 1 μg $DNA_5$; lane 2, $DNA_5$-affibody; lane 3, $DNA_6$-affibody; lane 4, $DNA_7$-affibody; lane 5, $DNA_8$-affibody.
Figures 8A, 8B:
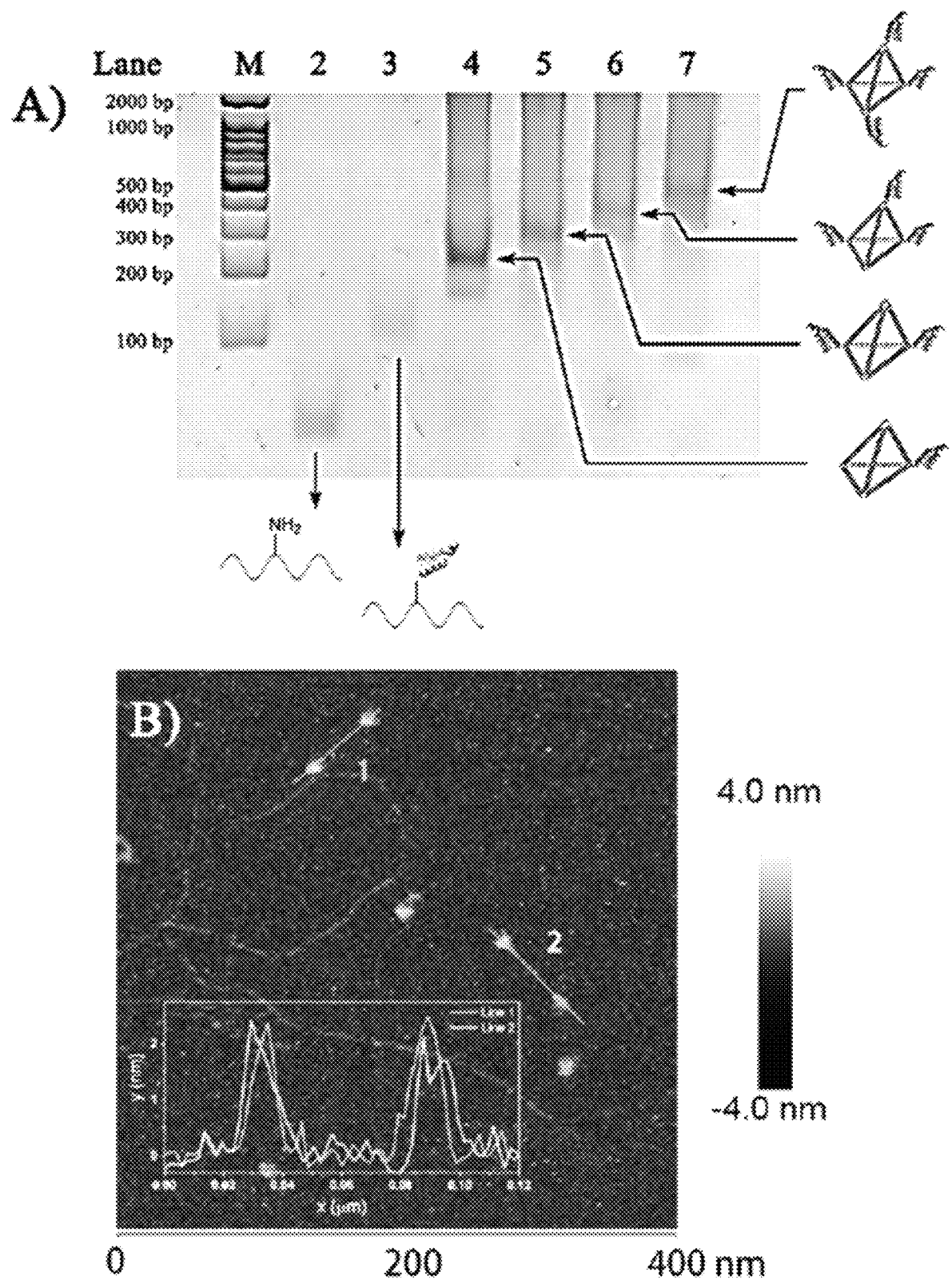
FIGS. 8A-8B show analysis of the structure of nanoparticles III and X.
Figure 9:
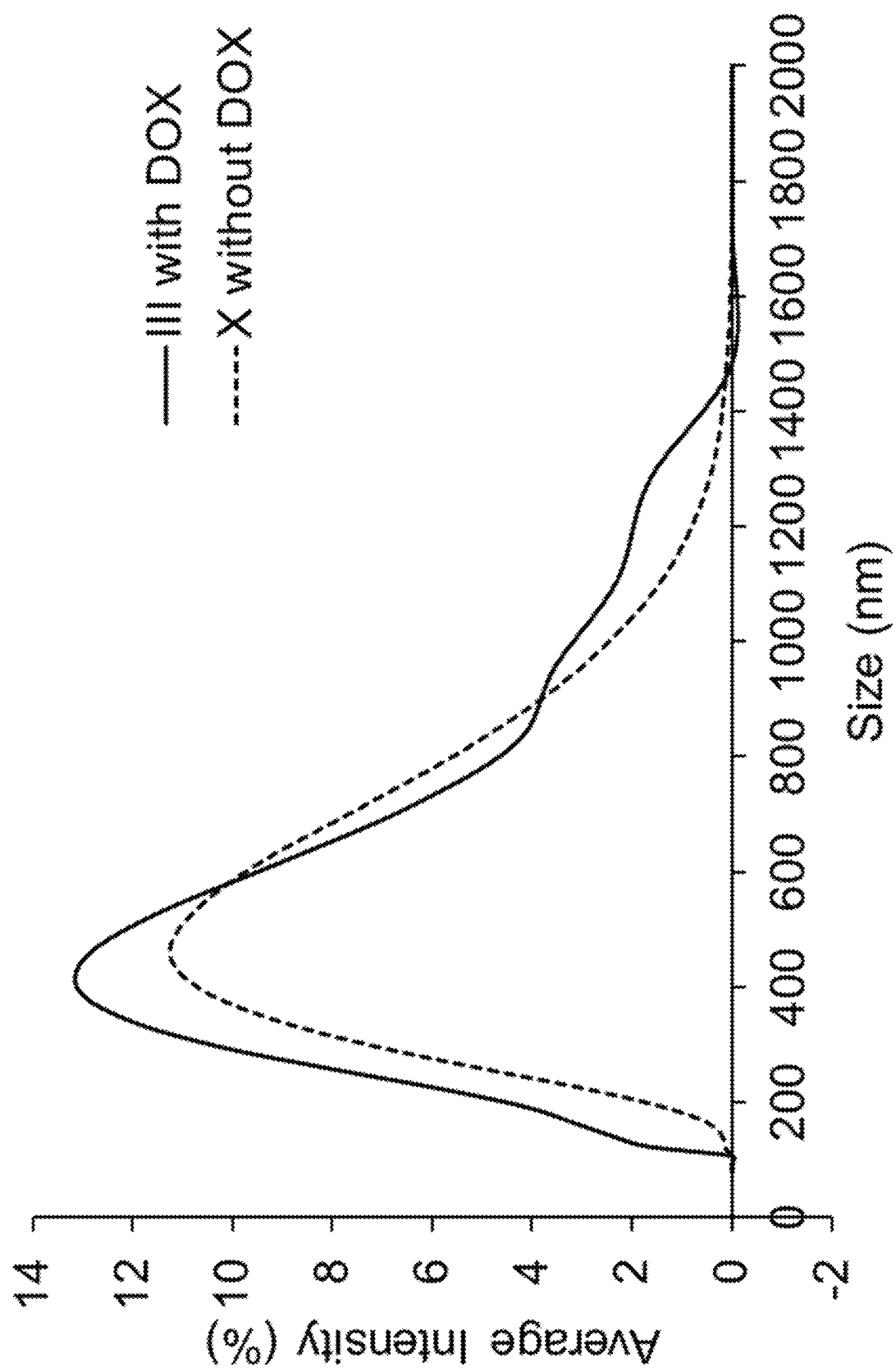
FIG. 9 shows hydrated particle size of nanoparticle X (without DOX) and III (containing DOX).

As shown in FIG. 20, four internal amino modified 63-nt single-strand DNAs ($DNA_{5-8}$) were treated with $N^\varepsilon$-malemidocaproyl-oxysuccinimide ester (EMCS) to obtain four $N^\varepsilon$-malemidocaproyloxy-DNAs ($VIII_{5-8}$). The obtained $VIII_{5-8}$ were treated with an affibody molecule containing a cysteine residue at its C-terminus to generate DNA-affibody chimeras ($IX_5$_8, FIG. 6). These four obtained DNA-affibody chimeras were purified using Ni-NTA chromatography, which specifically binds a hexahistidine peptide at the N-terminus of the affibody to remove the unreacted DNAs in the reaction mixture. The unreacted affibody in the eluate from Ni-NTA chromatography was removed using a DEAE-Sepharose CL-6B column that binds DNA efficiently. After purification chromatographically (FIG. 7), the purified four DNA-affibody chimeras were heated at 85° C. for 5 min and cooled to room temperature during 30 min to form nanoparticle X, which contained four affibody molecules, one at each of the four apexes of the DNA tetrahedron nanoparticle. The structure of nanoparticle X was characterized by 5% native polyacrylamide gel electrophoresis (FIG. 8A). To the obtained DNA nanostructure X was added excess doxorubicin and the mixture was incubated at room temperature for 10 min to generate the DNA tetrahedron-affibody-DOX nanoparticle (III). The DNA tetrahedron nanoparticle III was purified using a Sephadex G-25 column to remove excess unbound doxorubicin and the structure was verified by an atomic force microscopy (AFM, FIG. 8B).

Figure 10:
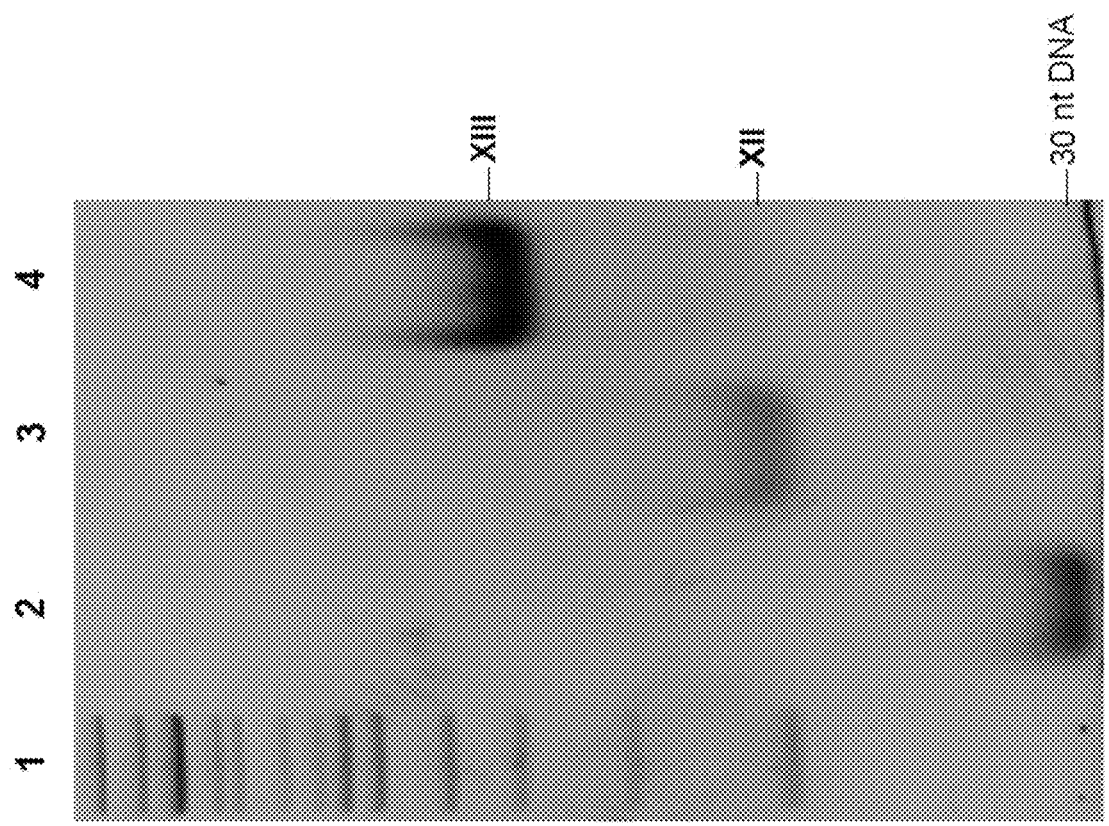
FIG. 10 shows analysis of the structure of nanoparticle XII and XIII using native 5% polyacrylamide gel electrophoresis. Lane 1, DNA marker (100 bp); lane 2, 30-nt $DNA_9$; lane 3, affibody-$DNA_9$ chimera (XII); lane 4, DNA nanoparticle containing 2 affibody molecules (XIII).

As shown in FIG. 21, two 5'-end amino modified 30-nt single-strand DNAs ($DNA_{9,10}$) were treated with $N^\varepsilon$-malemidocaproyl-oxysuccinimide ester (EMCS) to obtain two $N^\varepsilon$-malemidocaproyloxy-DNAs ($XI_{9,10}$). The obtained $XI_{9,10}$ was treated with an affibody molecule containing a cysteine residue at its C-terminus to generate DNA-affibody chimeras ($XII_{9,10}$). These two obtained DNA-affibody chimeras were purified using Ni-NTA chromatography, which specifically binds a hexahistidine peptide at the N-terminus of the affibody to remove the unreacted DNAs in the reaction mixture. The unreacted affibody in the eluate from Ni-NTA chromatography was removed using a DEAE-Sepharose CL-6B column that binds DNA efficiently. After purification chromatographically, the four purified DNA-affibody chimeras were heated at 85° C. for 5 min and cooled to room temperature during 30 min to form nanoparticle XIII. The structure of nanoparticle XIII was characterized by 5% native polyacrylamide gel electrophoresis (FIG. 10). To the obtained DNA nanostructure XIII was added excess doxorubicin and the mixture was incubated at room temperature for 10 min to generate the DNA tetrahedron-affibody-DOX nanoparticle (IV). The DNA tetrahedron nanoparticle IV was purified using a Sephadex G-25 column to remove excess unbound doxorubicin.

Figures 11A, 11B, 11C, 11D:
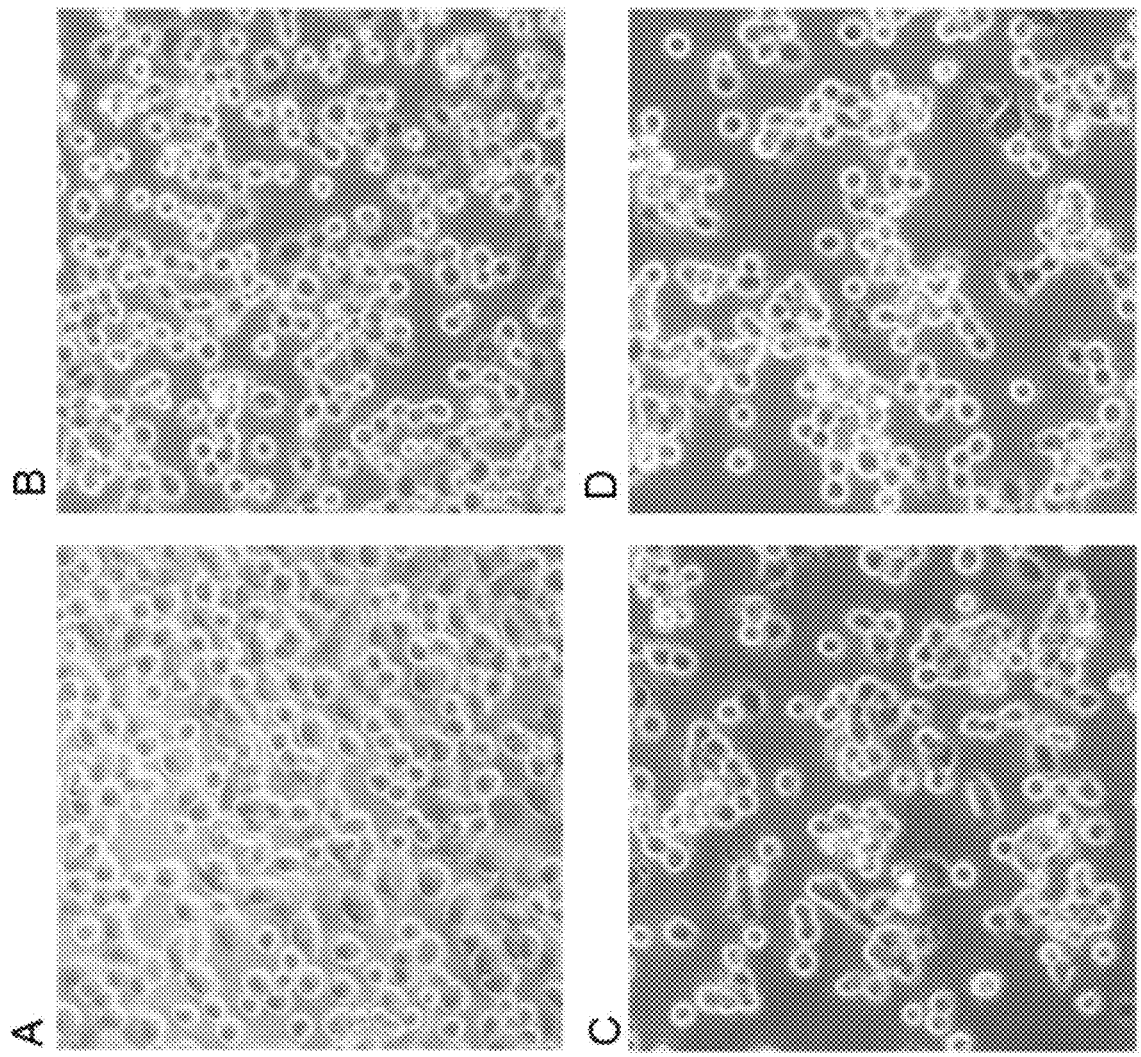
FIGS. 11A-11D show aggregation of BT474 cells induced by nanoparticles I, II and III.

In the presence of these nanoparticles, HER2+ breast cancer cells became covalently crosslinked to each other through multiple affibody-HER2 binding. These crosslinked cancer cells were bound together tightly, significantly decreasing the undesired dissociation of cells, thus preventing metastasis. To evaluate the ability of these DNA-affibody-DOX nanoparticles to crosslink HER2 overexpressing cancer cells, BT474 breast cancer cells were cultured at 37° C. for 24 h in the presence of 20 nM I-III or 100 nM IV (FIGS. 11A-11D and 12). As shown in FIGS. 11A-11D, the HER2+ BT474 cells without any drug treatment were not aggregated in the control group (FIG. 11A). Nanoparticle I contains two affibody molecules that are oriented in the same direction, and thus are more likely to bind twice to one cell than to crosslink adjacent cells. Therefore, little aggregation was induced by nanopaticle I (FIG. 11B). In comparison, each molecule of nanoparticle II and III contained four affibody molecules, oriented in a fashion that can bind to two adjacent cells; this resulted in significant cell aggregation (FIGS. 11C and 11D). As shown, HER2+ BT474 breast cancer cells were crosslinked to each other, forming multiple cell clusters in the presence of nanoparticles II and III. As shown in FIG. 12, the nanoparticle IV also crosslinked HER2+ BT474 breast cancer cells. In the crosslinked cancer cell clusters, the small molecule drugs in the nanoparticle released slowly, resulting in cancer cell apoptosis in 72 h.

Figure 13:
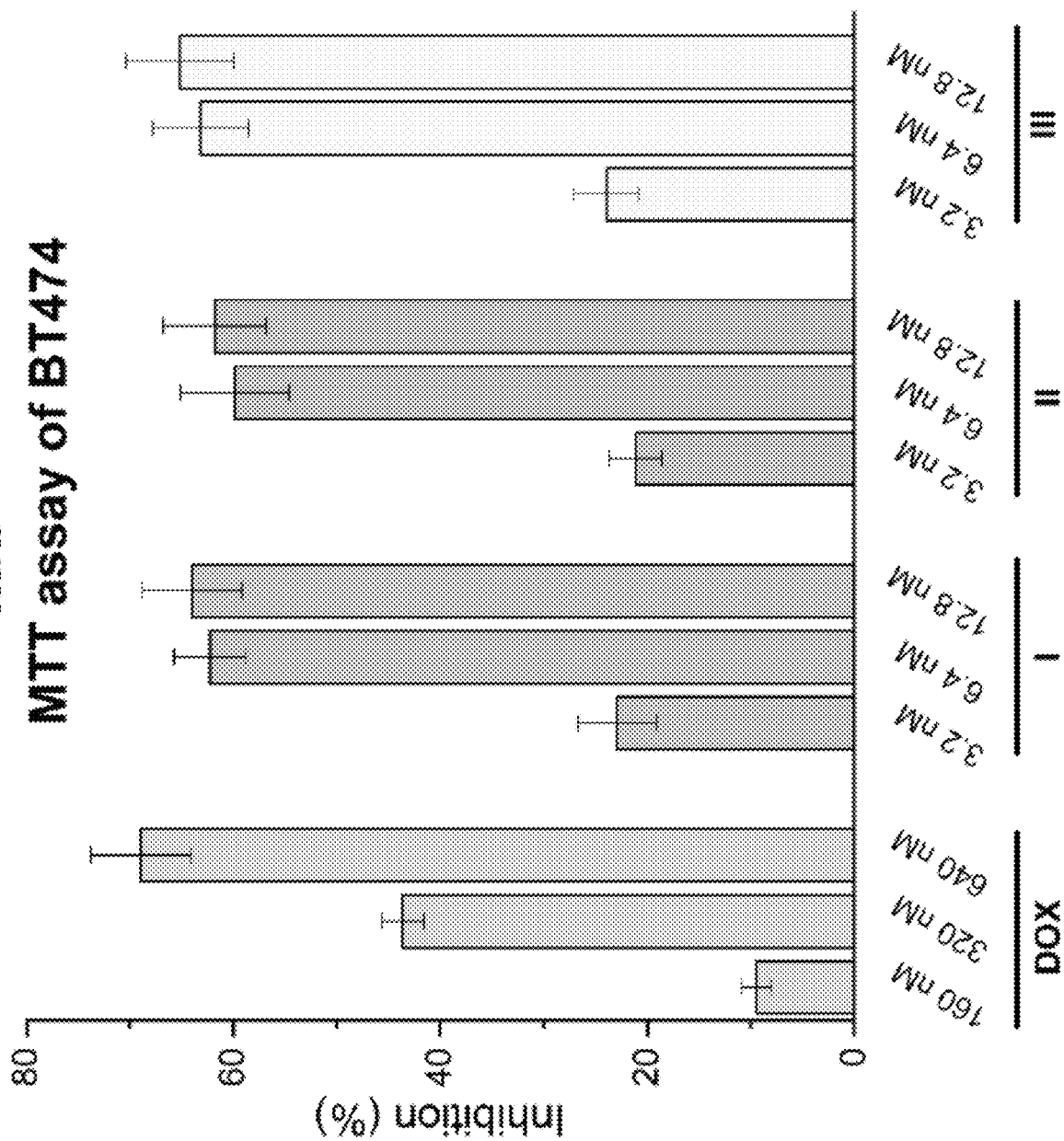
FIG. 13 shows inhibition of the cell growth of BT474 breast cancer cells by the DOX and DNA tetrahedron-affibody-DOX nanoparticles I-III. The ratio of DNA tetrahedron-affibody nanoparticles and DOX was 1:50 in nanoparticles I-III. Cell growth was measured using an MTT assay after 72 h treatment with DOX and nanoparticles I-III. The results are expressed as a percentage of the control with the means±standard deviation.
Figure 14:
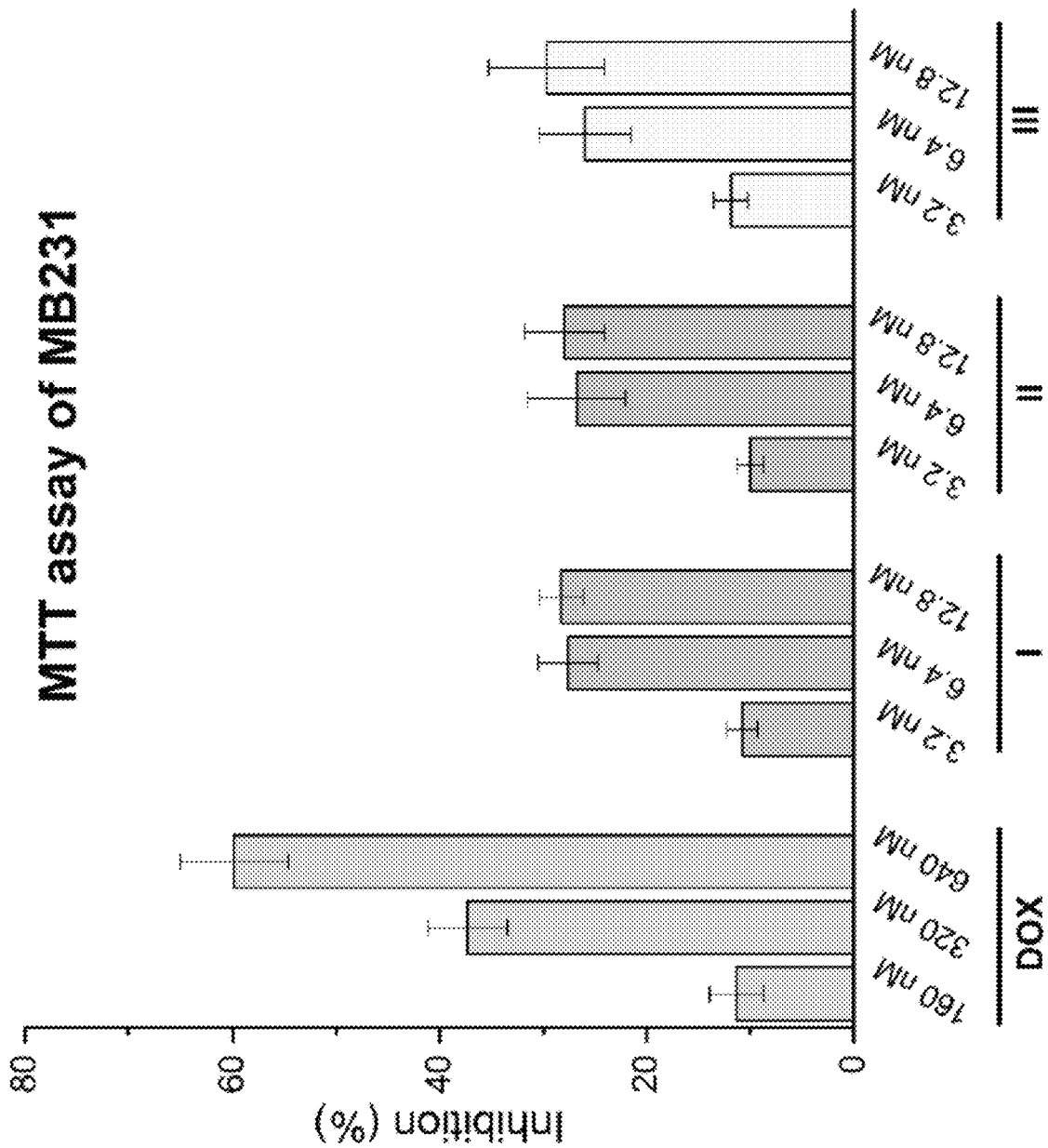
FIG. 14 shows inhibition of the cell growth of MDA-MB-231 breast cancer cells by the DOX and DNA tetrahedron-affibody-DOX nanoparticles I-III. The ratio of DNA tetrahedron-affibody nanoparticles and DOX was 1:50 in nanoparticles I-III. Cell growth was measured using an MTT assay after 72 h treatment with DOX and nanoparticles I-III. The results are expressed as a percentage of the control with the means±standard deviation.
Figure 15:
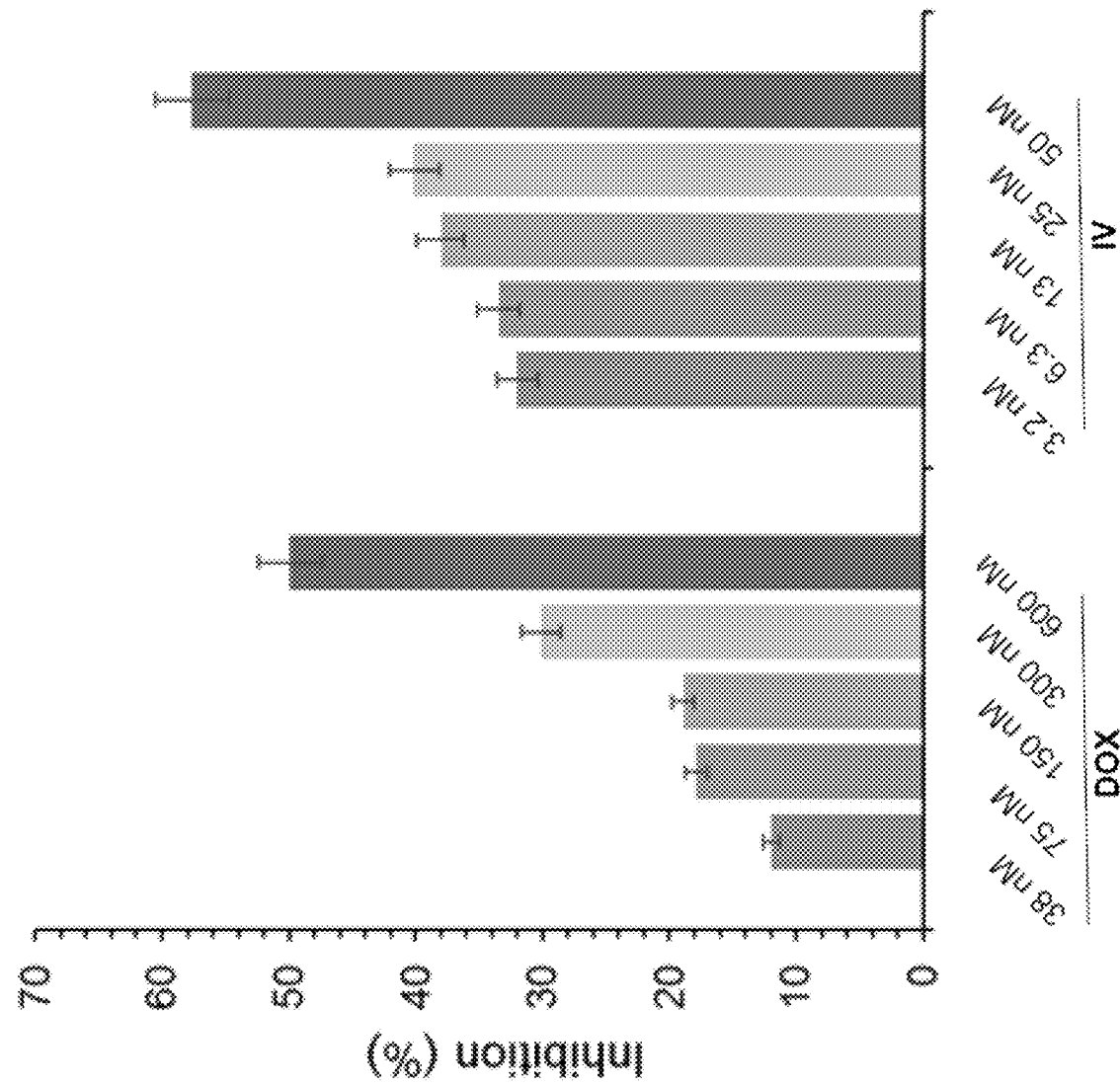
FIG. 15 shows inhibition of the cell growth of BT474 breast cancer cells by the DOX and IV. The ratio of DNA-affibody nanoparticles and DOX was 1:12 in nanoparticles IV. Cell growth was measured using an MTT assay after 72 h treatment with DOX and nanoparticles IV. The results are expressed as a percentage of the control with the means±standard deviation.

In an MTT assay, a HER2 receptor overexpressed breast cancer cell line BT474 and a HER2 low expressed breast cancer cell line MDA-MB-231 were used to evaluate the inhibition of the cell growth by nanoparticles I-IV. As shown in FIG. 13, nanoparticles I-III mediated same inhibition of the HER2 overexpressing breast cancer cells over the concentration range of 3-13 nM. However, all these three nanoparticles exhibited greater inhibition of the HER2 overexpressing breast cancer cells than doxorubin itself (with the same amount of doxorubin in the three samples) at low concentration. Especially at the lowest concentration (3 nM I-III vs 160 nM DOX), all three nanoparticles exhibited about two-fold greater inhibition toward BT474 cells than doxorubin. To the contrary, all three nanoparticles exhibited lesser inhibition of MDA-MB-231 breast cancer cells expressing HER2 at a lower level (FIG. 14). At the higher concentration (13 nM I-III vs 640 nM DOX), all nanoparticles displayed about two-fold lesser inhibition of MDA-MB-231 cells than doxorubin. As shown in FIG. 15, the nanoparticle IV exhibited greater inhibition of BT474 cells over the concentration range of 3-50 nM than doxorubin (over the concentration range of 38-600 nM). These results showed that all these DNA-affibody-DOX nanoparticles specifically target the HER2 receptor and exhibit greater selectivity in inhibiting HER2 overexpressing cancers cells than doxorubicin.

Figures 16A, 16B, 16C, 16D, 16E, 16F:
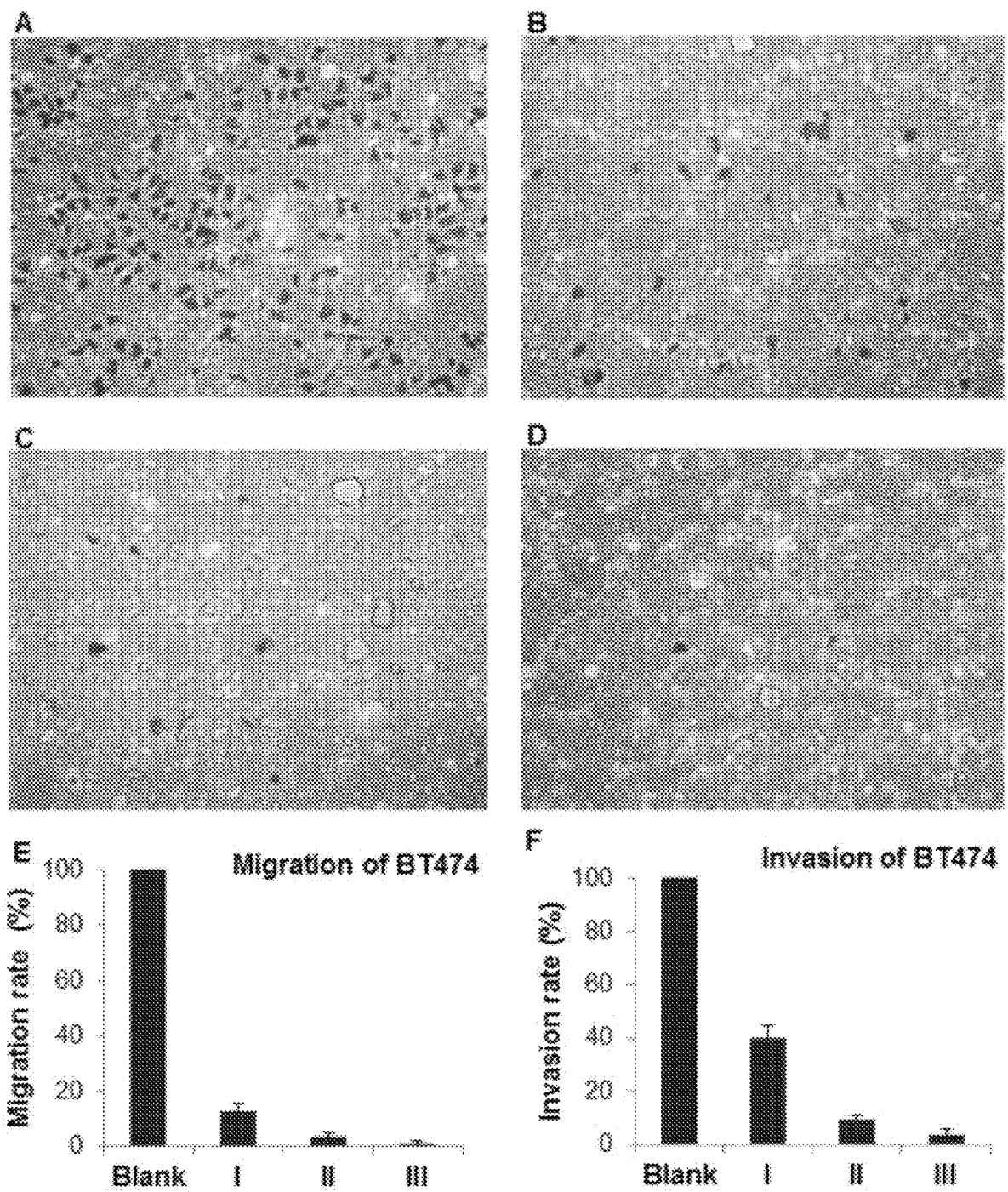
FIGS. 16A-16F show migration and invasion of BT474 cells.

Since nanoparticles II-IV can crosslink HER2 overexpressing cancer cells, they were expected to be able to block the progression of metastasis. A Transwell™ migration assay was used to evaluate their inhibition ability of nanoparticles II and III. As shown in FIGS. 16B and 16E, nanoparticle I inhibited the migration of BT474 cancer cells to the extent of 87% at 20 nM concentration because of its strong inhibition of cell growth (FIG. 13). Comparatively, nanoparticles II and III inhibited migration of BT474 cancer cells at the same concentration to the extent of 97% and 99%, respectively (FIGS. 16C-16E). Since these three nanoparticles exert almost the same inhibition of cell growth, the enhanced inhibition of migration by nanoparticles II and III are attributed to its ability to crosslink the cells. In an invasion assay using BT474 cells, a similar result was observed (FIG. 16F). Nanoparticle I inhibited the invasion of BT474 cancer cells to the extent of 60% at 20 nM concentration but nanoparticles II and III inhibited invasion to the extent of 91% and 96%, respectively at the same concentration. In nanoparticle II, four affibody molecules are located on four edges of the tetrahedron (having a total of six edges), which is a non-symmetrical structure. Comparatively, nanoparticle III contained four affibody molecules at its four apexes, which is symmetrical and blocked the metastasis of HER2+ cancer cells more efficiently. A Transwell™ invasion assay was also used to evaluate the inhibition ability of nanoparticles IV. As shown in FIG. 17, nanoparticle IV exhibited greater inhibition of the invasion of BT474 cancer cells than doxorubicin.

Figure 18:
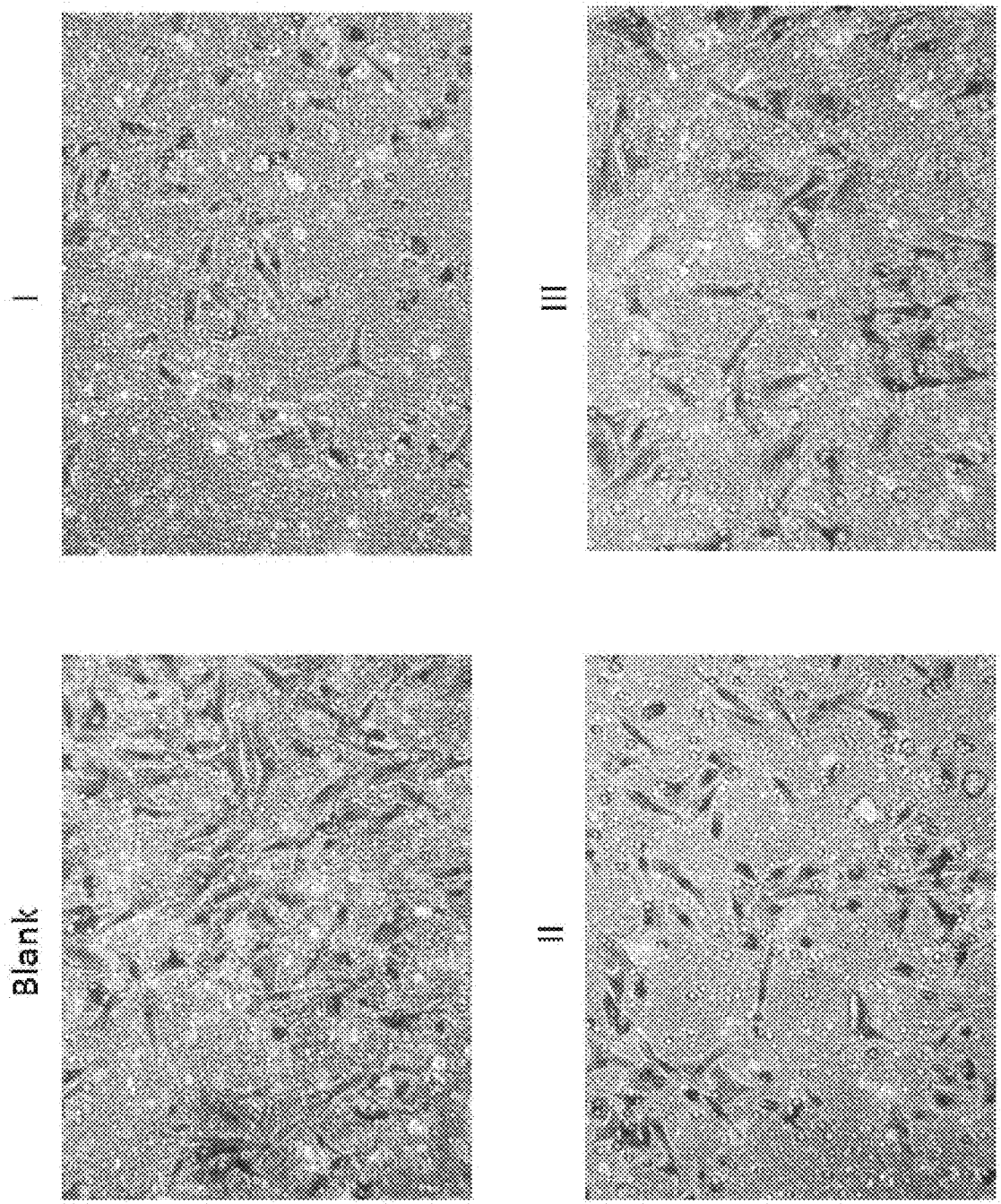
FIG. 18 shows migration of MB231 cells. Migrated MB231 cells without drug treatment; (I) Migrated MB231 cells in the presence of 20 nM nanoparticle I; (II) Migrated MB231 cells in the presence of 20 nM nanoparticle II; (III) Migrated MB231 cells in the presence of 20 nM nanoparticle III.

For cancer cells that highly overexpress HER2, nanoparticles II-IV crosslinked them and enhanced the inhibition of both migration and invasion. However, for cancer cells that overexpressed HER2 less abundantly, such as MDA-MB-231, the nanoparticles exhibited lower potential to crosslink them. As shown in FIG. 18, nanoparticles II and III had a low efficiency (16% and 40%) for inhibiting the migration of MDA-MB-231 cells.

Figure 22:
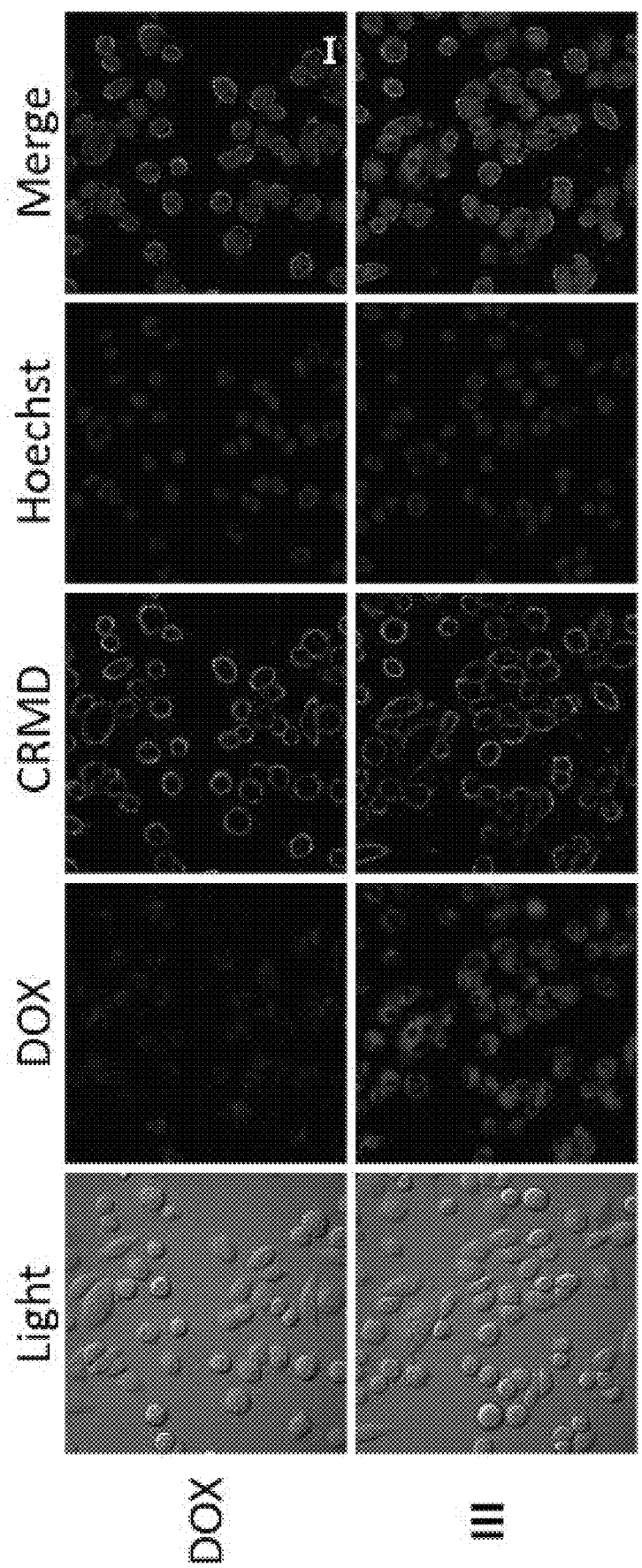
FIG. 22 shows a HER2 targeting assay in BT474 breast cancer cells. After addition of each agent (1 μM DOX, 0.02 μM III, 1×CellBrite red cytoplasmic membrane dye (CRMD), or 1×Hoechst 33342 fluorescent stain), samples were imaged with a Nikon C2 scanning confocal on a Nikon Ti microscope. Excitation lasers of 405 nm, 561 nm, and 640 nm were paired with DAPI, TRITC, and Cy5 channel detectors, respectively. Top panel, BT474 cells were treated with doxorubicin for 2 min; bottom panel, BT474 cells were treated with III for 2 min. Scale bar: 20 μm.

HER2 targeting assay—In this study, two DNA tetrahedron-affibody-DOX nanoparticles containing four affibody molecules (II and III) specifically targeted HER2 overexpressing cancer cells and crosslinked them, blocking their metastasis (FIG. 22). While II and III have similar cell growth inhibition and crosslinking abilities, III blocked cancer cell migration and invasion more efficiently than II. Therefore, nanoparticle III was used to verify HER2 targeting in a fluorescent cell imaging assay and a Western blot assay. In the fluorescent cell imaging assay, nanoparticle III containing DOX was added to the HER2 overexpressing BT474 cells for studying cell targeting. The fluorescence of DOX in the nanoparticle was used to image nanoparticle III; the fluorescence of CellBrite® red cytoplasmic membrane dye was used to image the cell membrane; and Hoechst 33342 fluorescent stain was used to image the nucleus. As shown in FIG. 22 (top panel), the control drug (DOX) entered BT474 cells in minutes. In comparison, nanoparticle III was targeted to HER2 overexpressing BT474 cells and efficiently delivered DOX into the cytoplasm. The fluorescent intensity of nanoparticle III in cells was at least 2-fold greater than that of the control DOX.

Figure 23:
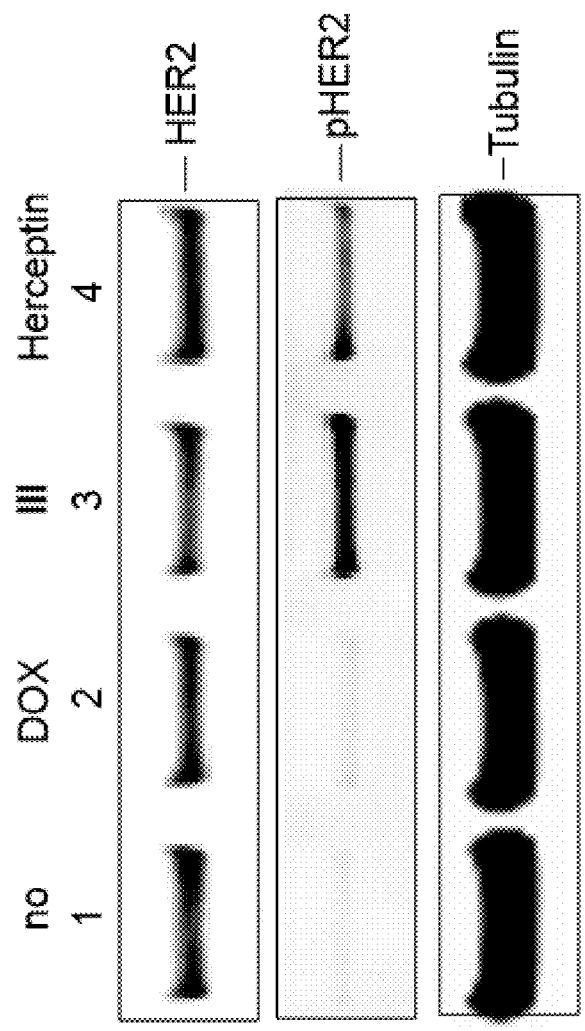
FIG. 23 shows a Western blot assay for HER2 targeting in BT474 cells. Lane 1, without treatment of any drug; lane 2, BT474 cells were treated with 1 μM DOX; lane 3, BT474 cells were treated with 0.02 μM III; lane 4, BT474 cells were treated with 1 μM Herceptin. The primary antibodies were HER2/ErbB2 rabbit Ab, phosphor-HER2/ErbB2 (Y1221/1222) rabbit mAb and anti-tubulin mouse mAb, respectively.

To verify that nanoparticle III specifically targeted the HER2 receptor, a Western blot assay was used for analysis of the HER2 level in BT474 cell samples. In a previous report, an antibody drug—Herceptin specifically targeted HER2 receptor and increased the phosphorylation of HER2 in 1 hour. Here, Herceptin was used as a positive control to evaluate the specific targeting of HER2 by nanoparticle III. After treatment with DOX, nanoparticle III and Herceptin for 1 hour, BT474 cells were collected and analyzed using HER2 antibody and phosphorylated HER2 (Y1221/1222) antibody, respectively. As shown in FIG. 23, all three treatments slightly decreased the level of HER2 protein. However, only nanoparticle III and the positive control, Herceptin, specifically increased the level of phosphorylated HER2 (Y1221/1222). Nanoparticle III had the greatest ability to induce the phosphorylation of HER2 receptor. Doxorubicin itself did not change the level of phosphorylated HER2 compared to the sample without any drug treatment.

In summary, the Examples demonstrate a strategy to crosslink HER2+ breast cancer cells together using a DNA tetrahedron-affibody-DOX nanoparticle. Two DNA tetrahedron-affibody-DOX nanoparticles contain four affibody molecules covalently coupled to four edges or apexes of a DNA tetrahedron and one linear double-strands DNA-affibody-doxorubicin nanoparticle contains two affibody molecules covalently coupled to two ends of the DNA were studied. All these nanoparticles are highly specific for HER2+ cells and cause the HER2 overexpressing cancer cells to be bound together tightly via crosslinking by the affibody molecules of the nanoparticle to prevent cancer cell metastasis. The reversibly bound drug was then delivered specifically to these cancer cells to induce apoptosis.

We claim:

1. A linear peptide-polynucleotide complex comprising two peptide-polynucleotide chimeras, each peptide-polynucleotide chimera comprising one or more human epidermal growth factor receptor (HER) binding peptides, a linker, and a single-stranded polynucleotide, wherein the single-stranded polynucleotide is selected from the group consisting of SEQ ID NO: 16 and SEQ ID NO:17.

2. The linear peptide-polynucleotide complex of claim 1, wherein the one or more HER binding peptides have a length of 10 amino acids to 1000 amino acids.

3. The linear peptide-polynucleotide complex of claim 2, wherein at least one of the one or more HER binding peptides is an affibody.

4. The linear peptide-polynucleotide complex of claim 3, wherein the affibody comprises amino acid sequence SEQ ID NO:5, wherein the two peptide-polynucleotide chimeras are complementary and form a double-helix structure, further comprising multiple molecules of a small molecule drug covalently or non-covalently bound to the peptide-polynucleotide complex.

5. The linear peptide-polynucleotide complex of claim 4, wherein the small molecule drug is selected from the group consisting of doxorubicin, daunorubicin, etoposide, camptothecin, cisplatin, mitomycin C, bleomycin, cyclophosphamide, 5-fluorouracil, hydroxyurea, cytosine arabinoside, and gemcitabine.

6. A method of treating a cancer associated with overexpression of a human epithelial growth factor receptor (HER), the method comprising administering a therapeutically effective amount of a pharmaceutical composition comprising the peptide-polynucleotide complex of claim 4 to a subject in need thereof, whereby administration of the composition treats a cancer associated with overexpression of HER.

7. The method of claim 6, wherein the cancer is selected from the group consisting of breast, ovarian, gastric, prostate, and lung cancer.

8. The method of claim 6, wherein the cancer is metastatic cancer.

9. The method of claim 6, wherein the cancer is a late-stage cancer.

10. The method of claim 6, wherein the method of administration is by injection or by a catheter in communication with a drug delivery pump.

11. A method of suppressing gene expression in target cells of a mammal, comprising the steps of administering a peptide-polynucleotide complex of claim 4, whereby administration of the complex suppresses expression of HER2 in the target cells.

12. A linear polynucleotide-affibody-drug complex comprising two DNA polynucleotides forming a double-helix structure, two affibody molecules, and multiple molecules of a small molecule drug covalently or non-covalently bound to the DNA double-helix structure, wherein the two DNA polynucleotides are selected from the group consisting of SEQ ID NO:16 and SEQ ID NO:17, wherein the two affibody molecules are located on opposite ends of the DNA double-helix structure.

13. The complex of claim 12, wherein the small molecule drug is selected from the group consisting of doxorubicin, daunorubicin, etoposide, camptothecin, cisplatin, mitomycin C, bleomycin, cyclophosphamide, 5-fluorouracil, hydroxyurea, cytosine arabinoside, and gemcitabine.

14. A composition comprising: a peptide-polynucleotide tetrahedron complex comprising four peptide-polynucleotide chimeras; and a linear peptide-polynucleotide complex comprising two peptide-polynucleotide chimeras, wherein each peptide-polynucleotide chimera comprises one or more human epidermal growth factor receptor (HER) binding peptides, a linker, and a single-stranded polynucleotide, wherein the single-stranded polynucleotide is selected from the group consisting of SEQ ID NO:16 and SEQ ID NO:17.

15. The composition of claim 14, wherein the one or more HER binding peptides have a length of 10 amino acids to 1000 amino acids.

16. The composition of claim 15, wherein at least one of the one or more HER binding peptides is an affibody.

17. The composition of claim 16, wherein the affibody comprises amino acid sequence SEQ ID NO:5.

18. The composition of claim 14, further comprising multiple molecules of a small molecule drug covalently or non-covalently bound to the peptide-polynucleotide tetrahedron complex and the linear peptide-polynucleotide complex.

* * * * *